US011519980B2

(12) United States Patent
Vincent et al.

(10) Patent No.: US 11,519,980 B2
(45) Date of Patent: Dec. 6, 2022

(54) CONTOURED RADIO FREQUENCY COIL ASSEMBLIES FOR A MAGNETIC RESONANCE SYSTEM

(71) Applicant: GE PRECISION HEALTHCARE LLC, Wauwatosa, WI (US)

(72) Inventors: Jana M. Vincent, Kent, OH (US); Victor Taracila, Orange Village, OH (US); Clyve Konrad R. Follante, Twinsburg, OH (US); Mark Giancola, Chesterland, OH (US); Yun-Jeong Stickle, Solon, OH (US); Fraser J. L. Robb, Aurora, OH (US); Robert Steven Stormont, Hartland, WI (US)

(73) Assignee: GE PRECISION HEALTHCARE LLC, Wauwatosa, WI (US)

( * ) Notice: Subject to any disclaimer, the term of this patent is extended or adjusted under 35 U.S.C. 154(b) by 0 days.

(21) Appl. No.: 17/231,435

(22) Filed: Apr. 15, 2021

(65) Prior Publication Data
US 2022/0334202 A1 Oct. 20, 2022

(51) Int. Cl.
*G01R 33/34* (2006.01)
*A61B 5/055* (2006.01)

(52) U.S. Cl.
CPC ........ *G01R 33/34092* (2013.01); *A61B 5/055* (2013.01); *G01R 33/34084* (2013.01)

(58) Field of Classification Search
CPC ........ G01R 33/34092; G01R 33/34084; A61B 5/055
See application file for complete search history.

(56) References Cited

U.S. PATENT DOCUMENTS

| 2005/0104591 | A1 | 5/2005 | Qu et al. |
| 2008/0174314 | A1 | 7/2008 | Holwell et al. |
| 2013/0137969 | A1 | 5/2013 | Jones |
| 2014/0091791 | A1 | 4/2014 | Bulumulla et al. |
| 2014/0197832 | A1 | 7/2014 | Driesel et al. |
| 2014/0200437 | A1 | 7/2014 | Yager et al. |
| 2015/0168515 | A1 | 6/2015 | Ishihara et al. |
| 2018/0335491 | A1 | 11/2018 | Yang et al. |
| 2019/0154774 | A1 | 5/2019 | Hushek et al. |
| 2019/0277926 | A1 | 9/2019 | Stormont et al. |

(Continued)

OTHER PUBLICATIONS

Vincent et al., "Ultra-Flexible, High-Resolution, 60-Channel RF Coil for Supine Breast Imaging," Dec. 16, 2020, 3 pages.

(Continued)

*Primary Examiner* — G. M. A. Hyder
(74) *Attorney, Agent, or Firm* — Armstrong Teasdale LLP

(57) ABSTRACT

A supine torso radio frequency (RF) coil assembly for a magnetic resonance (MR) system is provided. The RF coil assembly includes an RF coil array and a lining. The RF coil array includes a plurality of RF coils each RF coil including a coil loop that includes a wire conductor, the wire conductor formed into the coil loop and a coupling electronics portion coupled to the coil loop. The plurality of RF coils form into a contoured portion, the contoured portion sized to receive at least part of a breast of a subject therein. The lining includes a contoured portion. The RF coil array is coupled to and distributed on the lining, the contoured portion of the RF coil array covering and conforming with the contoured portion of the lining.

20 Claims, 21 Drawing Sheets

(56) References Cited

U.S. PATENT DOCUMENTS

| | | | |
|---|---|---|---|
| 2019/0293738 A1 | 9/2019 | Popescu | |
| 2019/0310328 A1 | 10/2019 | Fuqua et al. | |
| 2019/0310329 A1 | 10/2019 | Malik et al. | |
| 2019/0353722 A1* | 11/2019 | Stormont | G01R 33/3628 |
| 2019/0377040 A1 | 12/2019 | Stack et al. | |
| 2020/0093394 A1* | 3/2020 | Li | A61B 5/6831 |

OTHER PUBLICATIONS

Siu, Albert L., Screening for Breast Cancer: U.S. Preventive Services Task Force Recommendation Statement, Annuals of Internal Medicine, Feb. 16, 2016, vol. 164 No. 4, p. 279-296.

Euler-Chelpin et al.. Sensitivity of screening mammography by density and texture: a cohort study from a population-based screening program in Denmark, Breast Cancer Research, 2019, 21, article 111.

Carbonaro et al., Contrast enhanced breast MRI: spatial displacement from prone to supine patient's position, European Journal of Radiology, Jun. 2012, vol. 81, Issue 6, p. 771-774.

Satake et al., Prediction of prone-to-supine tumor displacement in the breastusing patient position change: investigation with prone MRI and supine CT, Breast Cancer, 2016, 23, p. 149-158.

Aribal et al., Supplementary abbreviated supine breast MRI following a standard prone breast MRI with single contrast administration: is it effective in detecting the initial contrast-enhancing lesions?, Diagn Interv Radiol, 2019, 25, p. 265-269.

Joukainen et al., Feasibility of mapping breast cancer with supine breast MRI in patients scheduled for oncoplastic surgery, European Radiology, 2019, 29, p. 1435-1443.

Rossman et al., Characterization of a new ultra-flexible low-profile RF receive coil technology, Proceedings ISMRM 2017, 763.

Vasanawala et al., Development and Clinical implementation of Very Light Weight and Highly Flexible AIR Technology Arrays, Proceedings ISMRM 2017, 755.

Wake et al., Design of a 3D Printed Patient-Specific Dual Compartment Breast Phantom, Proceedings of the ISMRM 2019, 4124.

Corea et al., Screen-printed flexible MRI receive coils, Nature Communications, Mar. 10, 2016, 7 pgs.

* cited by examiner

US 11,519,980 B2

CONTOURED RADIO FREQUENCY COIL ASSEMBLIES FOR A MAGNETIC RESONANCE SYSTEM

BACKGROUND

The field of the disclosure relates generally to a magnetic resonance (MR) system, and more particularly, to radio frequency (RF) coil assemblies for an MR system.

Magnetic resonance imaging (MRI) has proven useful in diagnosis of many diseases. MRI provides detailed images of soft tissues, abnormal tissues such as tumors, and other structures, which cannot be readily imaged by other imaging modalities, such as computed tomography (CT). Further, MRI operates without exposing patients to ionizing radiation experienced in modalities such as CT and x-rays.

Physical breast examinations, ultrasound-guided biopsy, and surgery are performed in the supine position. Physicians therefore prefer breast imaging to be in the same orientation for accuracy concerns during surgery. Conventional breast coils are bulky such that MR breast scanning is usually performed prone. Lying prone along pressure points on the chest is generally uncomfortable, especially for subjects with musculoskeletal weakness and advance age. Conventional prone coils are also not adjustable to allow a good fit of breasts therein. On the other hand, respiratory and motion artifacts are challenges posed for supine breast MR scans.

BRIEF DESCRIPTION

In one aspect, a supine torso radio frequency (RF) coil assembly for a magnetic resonance (MR) system is provided. The RF coil assembly includes an RF coil array and a lining. The RF coil array includes a plurality of RF coils each RF coil including a coil loop that includes a wire conductor, the wire conductor formed into the coil loop and a coupling electronics portion coupled to the coil loop. The plurality of RF coils form into a contoured portion, the contoured portion sized to receive at least part of a breast of a subject therein. The lining includes a contoured portion. The RF coil array is coupled to and distributed on the lining, the contoured portion of the RF coil array covering and conforming with the contoured portion of the lining.

In another aspect, an RF coil assembly for an MR system is provided. The RF coil assembly includes an RF coil array and a lining. The RF coil array includes a plurality of RF coils each RF coil including a coil loop that includes a wire conductor, the wire conductor formed into the coil loop and a coupling electronics portion electrically connected to the coil loop. The plurality of RF coils form into a contoured portion, the contoured portion sized to receive at least part of a curved anatomy of a subject therein. The lining includes a contoured portion. The RF coil array is coupled to and distributed on the lining, the contoured portion of the RF coil array covering and conforming with the contoured portion of the lining.

DRAWINGS

DETAILED DESCRIPTION

Figure 1:
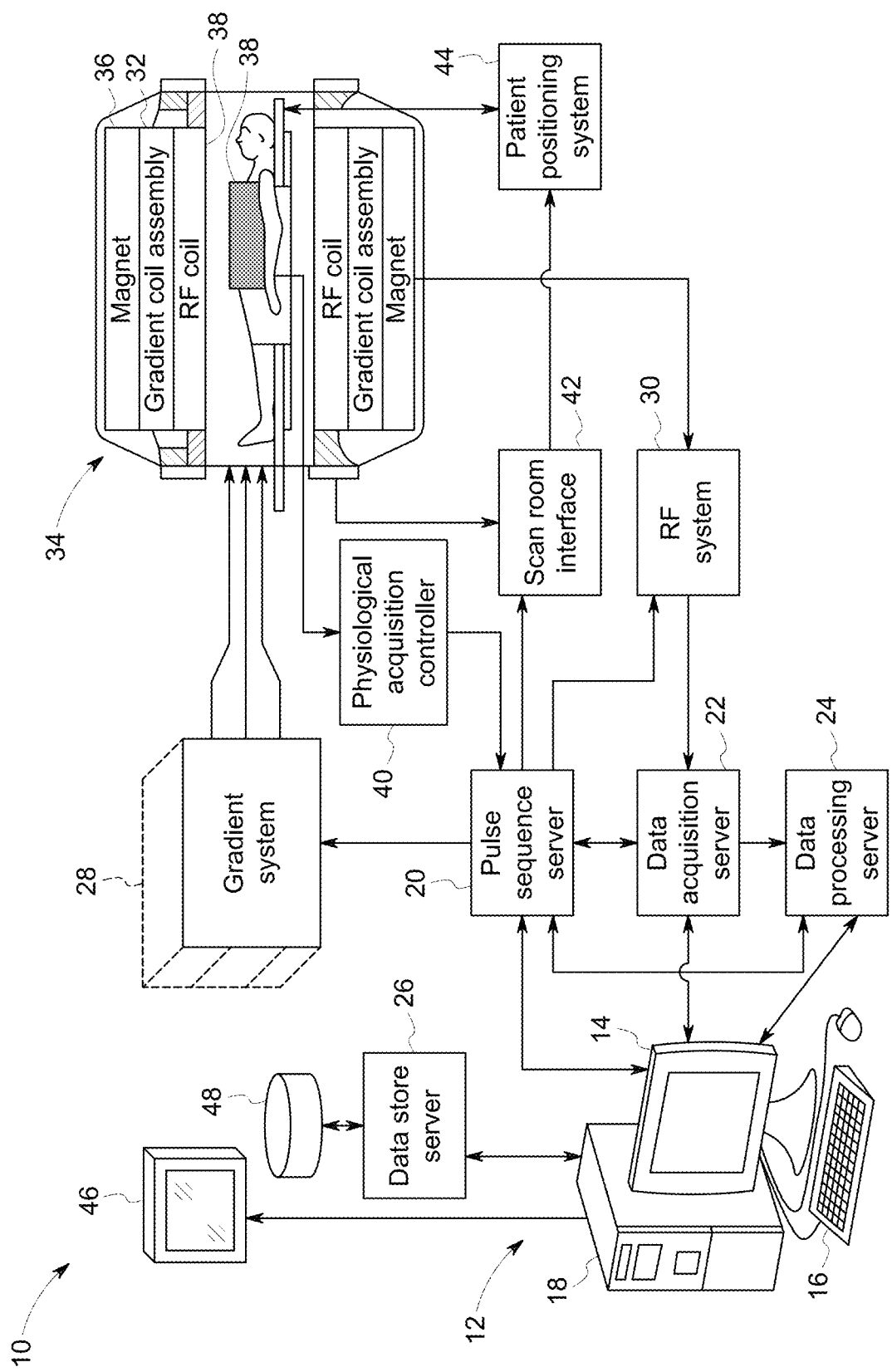
FIG. 1 is a block diagram of a magnetic resonance (MR) system.

The disclosure includes radio frequency (RF) coil assemblies for use in magnetic resonance (MR) systems in scanning curved areas of a subject's anatomy. As used herein, a subject is a human, an animal, a phantom, or any object scanned by an MR system. MR imaging is described as an example only. The assemblies, systems, and methods described herein may be used for MR spectroscopy. Method aspects of assembling and using the RF coil assemblies will be in part apparent and in part explicitly discussed in the following description.

While mammography, an X-ray imaging modality, remains as the conventional method for breast screening, MR has been shown to have greater sensitivity than mammography and is recommended for supplemental screening, especially in cases of human subjects with dense breast tissue or increased risk of breast cancer. Breast MR screenings are typically performed in the prone position, which allows for uncompressed tissue imaging and biopsy. However, physical breast examinations, ultrasound-guided biopsy, and surgery are performed in the supine position. The positional changes between prone and supine leads to changes in lesion localization, which is one of the challenges faced in surgical planning based on MR-detected lesions. There is also the challenge of coverage and subject comfort with existing prone RF coils. These coils are bulky and rigid, leading to discomfort along pressure points at the sternum with the former for the RF coil. Further, prone positioning is generally uncomfortable for subjects with musculoskeletal weakness, advanced age, or increased weight with pressure on the sternum. In addition, areas below the armpit and upper chest area such as level III axillary lymph nodes and supraclavicular lymph nodes are not always encompassed by the conventional coil. Supine breast imaging is advantageous in alleviating these discomforts while providing accurate positioning for surgical or radiation therapy planning. Supine breast imaging, however, faces challenges in reducing cardiac and respiratory motion artifacts caused by the weight of the coil pressing against the chest wall of the subject. The systems and methods described herein solve the problems above and provide a flexible, high-resolution, high-channel breast RF coils for subjects of various sizes. The RF coil assemblies disclosed herein are advantageously suitable for imaging of any curved anatomy of a subject such as the breast, torso, pelvis, pediatric head, or shoulder.

In MR imaging (MRI), a subject is placed in a magnet. When the subject is in the magnetic field generated by the magnet, magnetic moments of nuclei, such as protons, attempt to align with the magnetic field but precess about the magnetic field in a random order at the nuclei's Larmor frequency. The magnetic field of the magnet is referred to as B0 and extends in the longitudinal or z direction. In acquiring an MRI image, a magnetic field (referred to as an excitation field B1), which is in the x-y plane and near the Larmor frequency, is generated by a RF coil and may be used to rotate, or "tip," the net magnetic moment Mz of the nuclei from the z direction to the transverse or x-y plane. A signal, which is referred to as an MR signal, is emitted by the nuclei, after the excitation signal B1 is terminated. To use the MR signals to generate an image of a subject, magnetic field gradient pulses (Gx, Gy, and Gz) are used. The gradient pulses are used to scan through the k-space, the space of spatial frequencies or inverse of distances. A Fourier relationship exists between the acquired MR signals and an image of the subject, and therefore the image of the subject can be derived by reconstructing the MR signals.

FIG. 1 illustrates a schematic diagram of an exemplary MR system 10. In the exemplary embodiment, the MR system 10 includes a workstation 12 having a display 14 and a keyboard 16. The workstation 12 includes a processor 18, such as a commercially available programmable machine running a commercially available operating system. The workstation 12 provides an operator interface that allows scan prescriptions to be entered into the MR system 10. The workstation 12 is coupled to a pulse sequence server 20, a data acquisition server 22, a data processing server 24, and a data store server 26. The workstation 12 and each server 20, 22, 24, and 26 communicate with each other.

In the exemplary embodiment, the pulse sequence server 20 responds to instructions downloaded from the workstation 12 to operate a gradient system 28 and an RF system 30. The instructions are used to produce gradient and RF waveforms in MR pulse sequences. An RF coil 38 and a gradient coil assembly 32 are used to perform the prescribed MR pulse sequence. The RF coil 38 may be a whole body RF coil. The RF coil 38 may also be a local RF coil 38 that may be placed in proximity to the anatomy to be imaged, or a coil array that includes a plurality of coils.

In the exemplary embodiment, gradient waveforms used to perform the prescribed scan are produced and applied to the gradient system 28, which excites gradient coils in the gradient coil assembly 32 to produce the magnetic field gradients $G_x$, $G_y$, and $G_z$ used for position-encoding MR signals. The gradient coil assembly 32 forms part of a magnet assembly 34 that also includes a polarizing magnet 36 and the RF coil 38.

In the exemplary embodiment, the RF system 30 includes an RF transmitter for producing RF pulses used in MR pulse sequences. The RF transmitter is responsive to the scan prescription and direction from the pulse sequence server 20 to produce RF pulses of a desired frequency, phase, and pulse amplitude waveform. The generated RF pulses may be applied to the RF coil 38 by the RF system 30. Responsive MR signals detected by the RF coil 38 are received by the RF system 30, amplified, demodulated, filtered, and digitized under direction of commands produced by the pulse sequence server 20. The RF coil 38 is described as a transmit and receive coil such that the RF coil 38 transmits RF pulses and detects MR signals. In one embodiment, the MR system 10 may include a transmit RF coil that transmits RF pulses and a separate receive coil that detects MR signals. A transmission channel of the RF system 30 may be connected to a RF transmit coil and a receiver channel may be connected to a separate RF receive coil. Often, the transmission channel is connected to the whole body RF coil 38 and each receiver section is connected to a separate local RF coil.

In the exemplary embodiment, the RF system 30 also includes one or more RF receiver channels. Each RF receiver channel includes an RF amplifier that amplifies the MR signal received by the RF coil 38 to which the channel is connected, and a detector that detects and digitizes the I and Q quadrature components of the received MR signal. The magnitude of the received MR signal may then be determined as the square root of the sum of the squares of the I and Q components as in Eq. (1) below:

$$M=\sqrt{I^2+Q^2} \qquad (1);$$

and the phase of the received MR signal may also be determined as in Eq. (2) below:

$$\varphi = \tan^{-1}\left(\frac{Q}{I}\right). \qquad (2)$$

In the exemplary embodiment, the digitized MR signal samples produced by the RF system 30 are received by the data acquisition server 22. The data acquisition server 22 may operate in response to instructions downloaded from the workstation 12 to receive real-time MR data and provide buffer storage such that no data is lost by data overrun. In some scans, the data acquisition server 22 does little more than pass the acquired MR data to the data processing server 24. In scans that need information derived from acquired MR data to control further performance of the scan, however, the data acquisition server 22 is programmed to produce the needed information and convey it to the pulse sequence server 20. For example, during prescans, MR data is acquired and used to calibrate the pulse sequence performed by the pulse sequence server 20. Also, navigator signals may be acquired during a scan and used to adjust the operating parameters of the RF system 30 or the gradient system 28, or to control the view order in which k-space is sampled.

In the exemplary embodiment, the data processing server 24 receives MR data from the data acquisition server 22 and processes it in accordance with instructions downloaded from the workstation 12. Such processing may include, for example, Fourier transformation of raw k-space MR data to produce two or three-dimensional images, the application of filters to a reconstructed image, the performance of a back-projection image reconstruction of acquired MR data, the generation of functional MR images, and the calculation of motion or flow images.

In the exemplary embodiment, images reconstructed by the data processing server 24 are conveyed back to, and stored at, the workstation 12. In some embodiments, real-time images are stored in a database memory cache (not shown in FIG. 1), from which they may be output to operator display 14 or a display 46 that is located near the magnet assembly 34 for use by attending physicians. Batch mode images or selected real time images may be stored in a host database on disc storage 48 or on a cloud. When such images have been reconstructed and transferred to storage, the data processing server 24 notifies the data store server 26. The workstation 12 may be used by an operator to archive the images, produce films, or send the images via a network to other facilities.

During a scan, RF coil array interfacing cables (not shown) may be used to transmit signals between the RF coil 38 and other aspects of the MR system 10 (e.g., data acquisition server 22 and pulse sequence server 20), for example to control the RF coils and/or to receive signals from the RF coils. As described above, the RF coil 38 may be a transmit coil that transmits RF excitation signals, or a receive coil that receives the MR signals emitted by the subject. In an example, the transmit and receive coils are a single mechanical and electrical structure or array of structures, with transmit/receive mode switchable by auxiliary circuitry. In other examples, a transmit coil and a receive coil may be independent structures that are physically coupled to each other via the RF system 30. For enhanced image quality, however, a receive coil is desirable to be mechanically and electrically isolated from the transmit coil. In such cases, the receive coil in the receive mode is electromagnetically coupled to and resonant with an RF "echo" that is stimulated by the transmit coil. On the other hand, during a transmit mode, the receive coil is electromagnetically decoupled from and therefore not resonant with the transmit coil, during transmission of the RF signal. Such decoupling averts a potential problem of noise produced within the auxiliary circuitry when the receive coil couples to the full power of the RF signal. Additional details regarding the uncoupling of the receive RF coil will be described below.

A traditional receive coil for MR includes several conductive intervals joined between themselves by capacitors. By adjusting the capacitors' values, the impedance of the RF coil may be brought to its minimal value, usually characterized by a low resistance. At a resonant frequency, stored magnetic and electric energy alternate periodically. Each conductive interval, due to its length and width, possesses a certain self-capacitance, where electric energy is periodically stored as static electricity. The distribution of this electricity takes place over the entire conductive interval length in the order of 5-15 cm, causing similar range electric dipole field. In proximity of a large dielectric load, self-capacitance of the intervals change, resulting in detuning of the coil. In case of a lossy dielectric, dipole electric field causes Joule dissipation characterized by an increase overall resistance observed by the coil.

Traditional RF coils may include acid etched copper traces or loops on printed circuit boards (PCBs) with lumped electronic components (e.g., capacitors, inductors, baluns, and resisters), matching circuitry, decoupling circuitry, and pre-amplifiers. Such a configuration is typically bulky, heavy and rigid, and requires relatively strict placement of the coils relative to each other in an array to prevent coupling interactions among coil elements that may degrade image quality. As such, traditional RF coils and RF coil arrays lack flexibility and hence may not conform to subject anatomy, degrading imaging quality and subject comfort.

The RF coil used in the RF coil assemblies described herein includes a coil loop formed by wire conductors. In the case of two RF coils overlapping, the coupling electronics portion that couples with the coil loop of the RF coil has high blocking or source impedance, thereby minimizing mutual inductance coupling. Thin cross-sections of the wire conductor in the RF coil reduces the parasitic capacitance at the cross-overs or overlaps, and reduces other coupling such as electric field coupling and eddy current, in comparison to two traditional trace-based loops. The combination of high blocking impedance and thin cross-sections of the RF coil loop allows flexible placement of multiple coils into one RF coil assemblies over a finite area, while coupling between the RF coils is minimized and critical overlap between two loops is not required. Wire conductors also add flexibility to the coils, allowing the coil assembly to conform with a curved anatomy of a subject.

Figure 2:
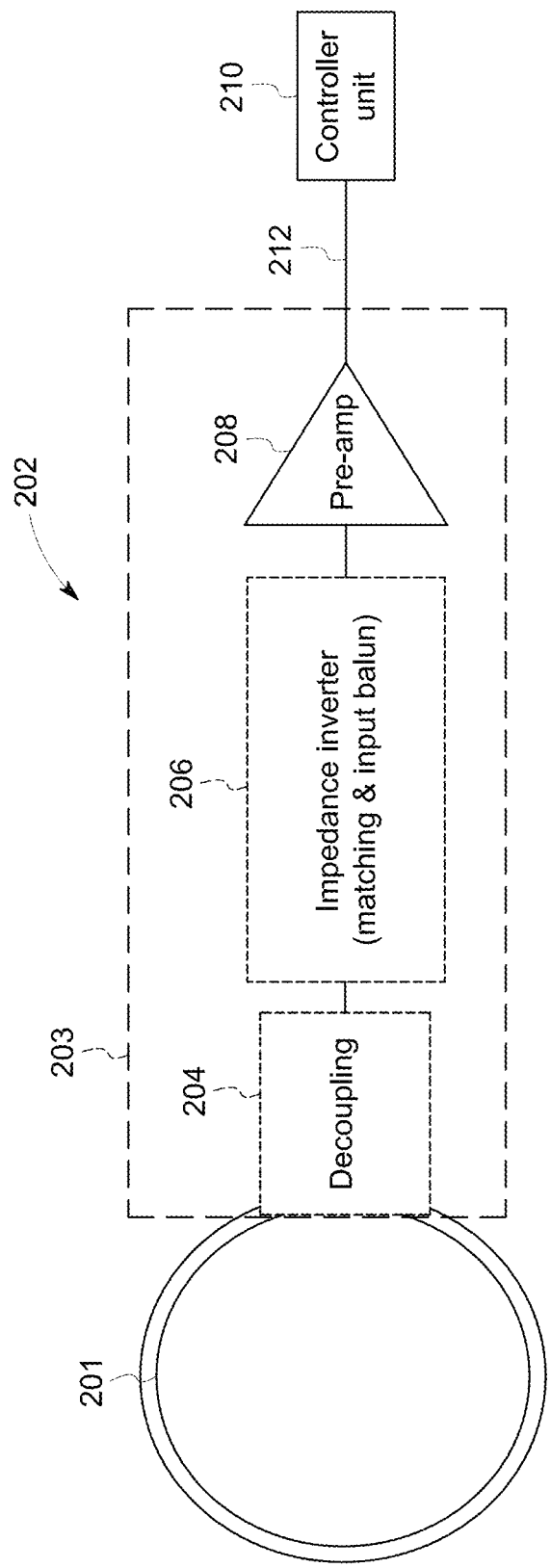
FIG. 2 is a block diagram of an exemplary radio frequency (RF) coil.

Turning now to FIG. 2, a schematic view of an RF coil 202 that includes a coil loop 201 coupled to a controller unit 210 via a coupling electronics portion 203 and a coil-interfacing cable 212 is shown. In one example, the RF coil may be a surface receive coil, which may be single- or multi-channeled. The RF coil 202 may operate at one or more frequencies in the MR system 10. The coil-interfacing cable 212 may be a coil-interfacing cable extending between the coupling electronics portion 203 and an interfacing connector of an RF coil array or an RF coil array interfacing cable extending between the interfacing connector of the RF coil array and other components of the MR system 10 such as the RF system 30.

Two coil loops can couple magnetically and electrically. One form of coupling is mutual inductance where signal and noise are transferred from one coil loop to another. The mutual inductance may be reduced by overlapping the coil loops. The mutual inductance may also be reduced by using a high blocking impedance in the coupling electronics portion. The blocking impedance $R_{block}$ seen by the coil loop in general depends on the resistance R of the coil loop, matching characteristic impedance $Z_0$ of the transmission line, and input impedance of the LNA (a linear amplifier or preamplifier) $R_{lna}$ and may be approximated as:

$$R_{block} = \frac{Z_0 R}{R_{lna}}.$$

When a relatively-high blocking impedance $R_{block}$ is used, $$\frac{X_L}{R} \le \frac{Z_0}{R_{lna}}$$

and the induced current from one coil loop to another is minimized, where $X_L = \omega_0 L$ is the reactance of the coil loop at the resonance frequency of the coil loop.

Other coupling such as coupling through electric field and eddy current may be minimized by reducing the cross-section of the wire conductor in the coil loop 201.

The coupling electronics portion 203 may be coupled to the coil loop 201 of the RF coil 202. Herein, the coupling electronics portion 203 may include a decoupling circuit 204, impedance inverter circuit 206, and a pre-amplifier 208. The decoupling circuit 204 may effectively decouple the RF coil during a transmit operation. Typically, the RF coil 202 in the receive mode may be coupled to a body of a subject being imaged by the MR system 10 in order to receive echoes of the RF signal transmitted during the transmit mode. If the RF coil 202 is not used for transmission, the RF coil 202 is decoupled from the RF transmit coil such as the RF body coil while the RF transmit coil is transmitting the RF signal. The decoupling of the receive coil from the transmit coil may be achieved using resonance circuits and PIN diodes, microelectromechanical systems (MEMS) switches, or another type of switching circuitry. Herein, the switching circuitry may activate detuning circuits operatively connected to the RF coil 202.

The impedance inverter circuit 206 may form an impedance matching network between the RF coil 202 and the pre-amplifier 208. The impedance inverter circuit 206 is configured to transform a coil impedance of the RF coil 202 into an optimal source of impedance for the pre-amplifier 208. The impedance inverter circuit 206 may include an impedance matching network and an input balun. The pre-amplifier 208 receives MR signals from the corresponding RF coil 202 and amplifies the received MR signals. In one example, the pre-amplifier may have a low input impedance that is configured to accommodate a relatively high blocking or source impedance. Additional details regarding the RF coil and associated coupling electronics portion will be explained in more detail below with respect to FIGS. 3A, 3B, 4A, and 4B. The coupling electronics portion 203 may be packaged in a small PCB with a surface area of approximately 2 cm² or smaller. The PCB may be protected with a conformal coating or an encapsulating resin.

The coil-interfacing cable 212, such as a RF coil array interfacing cable, may be used to transmit signals between the RF coils and other aspects of MR system 10. The RF coil array interfacing cables may be disposed within the bore or imaging space of the MR system 10 and subjected to electro-magnetic fields produced and used by the MR system 10. In MR systems, coil-interfacing cables, such as coil-interfacing cable 212, may support transmitter-driven common-mode currents, which may in turn create field distortions and/or unpredictable heating of components. Typically, common-mode currents are blocked by using baluns. Baluns or common-mode traps provide high common-mode impedances, which in turn reduces the effect of transmitter-driven currents.

Thus, coil-interfacing cable 212 may include one or more baluns. In traditional coil-interfacing cables, baluns are positioned with a relatively high density, as high dissipation/voltages may develop if the balun density is too low or if baluns are positioned at an inappropriate location. However, this dense placement may adversely affect flexibility, cost, and performance. As such, the one or more baluns in the coil-interfacing cable may be continuous baluns to ensure no high currents or standing waves, independent of positioning. The continuous baluns may be distributed, flutter, and/or butterfly baluns.

Figure 3A:
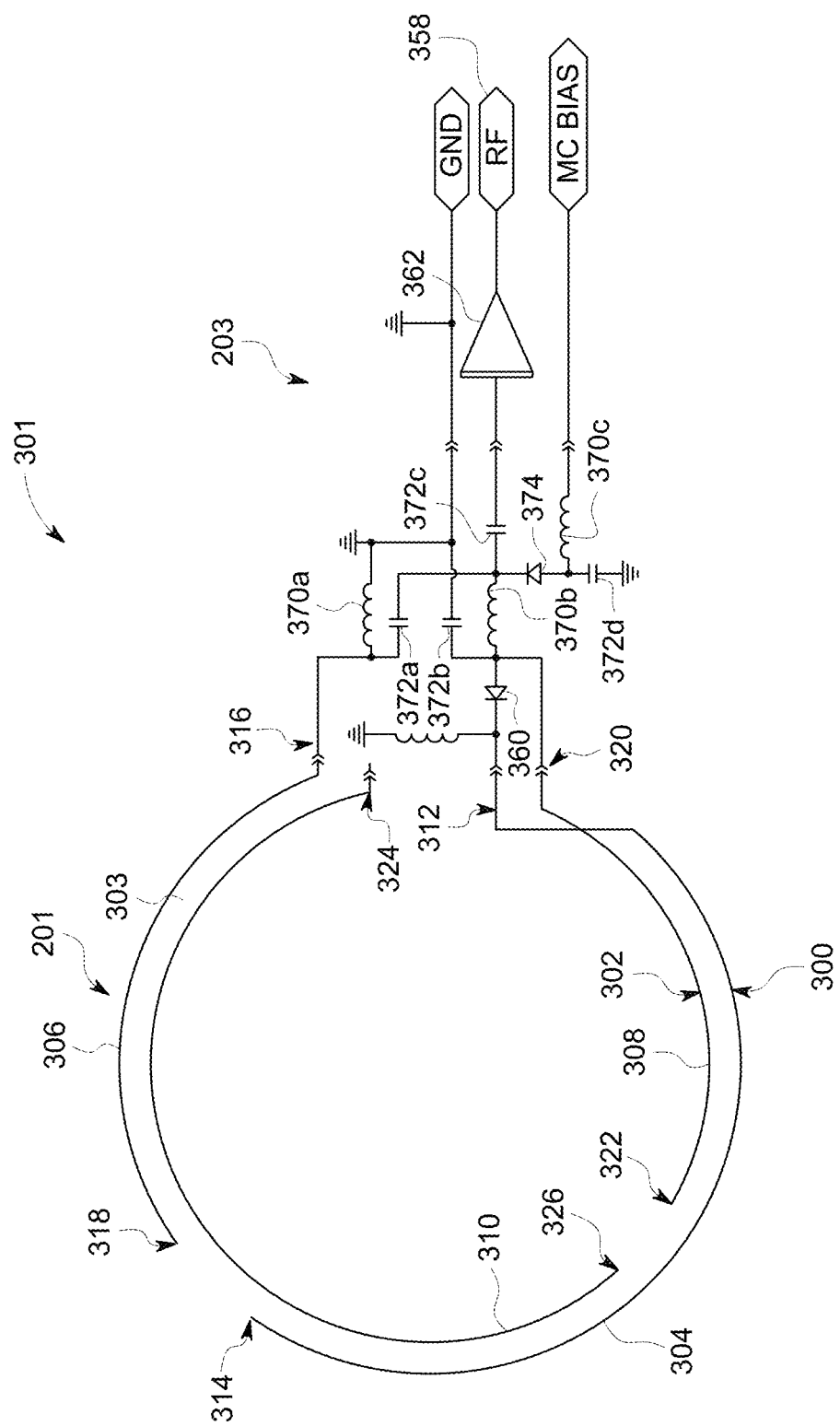
FIG. 3A is a schematic diagram of an exemplary RF coil shown in FIG. 2.

FIG. 3A is a schematic of an RF coil 301 having segmented conductors formed in accordance with an embodiment. RF coil 301 is a non-limiting example of RF coil 202 of FIG. 2 and as such includes coil loop 201 and coupling electronics portion 203 of RF coil 202. The coupling electronics portion allows the RF coil to transmit and/or receive RF signals when driven by the RF system 30 (shown in FIG. 1). In the illustrated embodiment, the RF coil 301 includes a first conductor 300 and a second conductor 302. The first and second conductors 300, 302 may be segmented such that the conductors form an open circuit (e.g., form a monopole). The segments of the conductors 300, 302 may have different lengths. The length of the first and second conductors 300, 302 may be varied to achieve a select distributed capacitance, and accordingly, a select resonance frequency.

The first conductor 300 includes a first segment 304 and a second segment 306. The first segment 304 includes a driven end 312 at an interface terminating to coupling electronics portion 203, which will be described in more detail below. The first segment 304 also includes a floating end 314 that is detached from a reference ground, thereby maintaining a floating state. The second segment 306 includes a driven end 316 at the interface terminating to the coupling electronics portion and a floating end 318 that is detached from a reference ground.

The second conductor 302 includes a first segment 308 and a second segment 310. The first segment 308 includes a driven end 320 at the interface. The first segment 308 also includes a floating end 322 that is detached from a reference ground, thereby maintaining a floating state. The second segment 310 includes a driven end 324 at the interface, and a floating end 326 that is detached from a reference ground. The driven end 324 may terminate at the interface such that end 324 is only coupled to the first conductor through the distributed capacitance. The capacitors shown around the loop between the conductors represent the capacitance between the wire conductors.

Distributed capacitance (DCAP), as used herein, represents a capacitance exhibited between conductors that grows evenly and uniformly along the length of the conductors and is void of discrete or lumped capacitive components and discrete or lumped inductive components. In the examples herein, the capacitance may grow in a uniform manner along the length of the first and second conductors 300, 302. For example, the first conductor 300 exhibits a distributed capacitance that grows based on the length of the first and second segments 304, 306. The second conductor 302 exhibits a distributed capacitance that grows based on the length of the first and second segments 308, 310. The first segments 304, 308 may have a different length than the second segments 306, 310. The relative difference in length between the first segments 304, 308 and the second segments 306, 310 may be used to produce an effective LC circuit have a resonance frequency at the desired center frequency. For example, by varying the length of the first segments 304, 308 relative to the lengths of the second segments 306, 310, an integrated distributed capacitance may be varied.

In the illustrated embodiment, the first and second wire conductors 300, 302 are shaped into a coil loop that terminates to an interface. But in other embodiments, other shapes are possible. For example, the coil loop may be a polygon, shaped to conform the contours of a surface (e.g., housing), and/or the like. The coil loop defines a conductive pathway along the first and second conductors. The first and second conductors are void of any discrete or lumped capacitive or inductive elements along an entire length of the conductive pathway. The coil loop may also include loops of varying gauge of stranded or solid conductor wire, loops of varying diameters with varying lengths of the first and second conductors 300, 302, and/or loops of varying spacing between the first and second conductors. For example, each of the first and second conductors may have no cuts or gaps (no segmented conductors) or one or more cuts or gaps (segmented conductors) at various locations along the conductive pathway.

A dielectric material 303 encapsulates and separates the first and second conductors 300, 302. The dielectric material 303 may be selectively chosen to achieve a select distributive capacitance. The dielectric material 303 may be based on a desired permittivity E to vary the effective capacitance of the coil loop. For example, the dielectric material 303 may be air, rubber, plastic, or any other dielectric material. In one example, the dielectric material may be polytetrafluoroethylene (pTFE). For example, the dielectric material 303 may be an insulating material surrounding the parallel conductive elements of the first and second conductors 300, 302. Alternatively, the first and second conductors 300, 302 may be twisted upon one another to from a twisted pair cable. As another example, the dielectric material 303 may be a plastic material. The first and second conductors 300, 302 may form a coaxial structure in which the plastic dielectric material 303 separates the first and second conductors. As another example, the first and second conductors may be configured as planar strips.

The coupling electronics portion 203 is operably and communicatively coupled to the RF system 30 to allow the RF coil 301 to transmit and/or receive RF signals. In the illustrated embodiment, the coupling electronics portion 203 includes a signal interface 358 configured to transmit and receive the RF signals. The signal interface 358 may transmit and receive the RF signals via a cable. The cable may be a 3-conductor triaxial cable having a center conductor, an inner shield, and an outer shield. The center conductor is connected to the RF signal and pre-amp control (RF), the inner shield is connected to ground (GND), and the outer shield is connected to the multi-control bias (diode decoupling control) (MC BIAS). A 10V power connection may be carried on the same conductor as the RF signal.

As explained above with respect to FIG. 2, the coupling electronics portion 203 includes a decoupling circuit, impedance inverter circuit, and pre-amplifier. As illustrated in FIG. 3A, the decoupling circuit includes a decoupling diode 360. The decoupling diode 360 may be provided with voltage from MC BIAS, for example, in order to turn decoupling diode 360 on. When on, decoupling diode 360 causes conductor 300 to short with conductor 302, thus causing the coil be off-resonance and hence decouple the coil during a transmit operation, for example.

The impedance inverter circuit includes a plurality of inductors, including first inductor 370a, second inductor 370b, and third inductor 370c; a plurality of capacitors, including first capacitor 372a, a second capacitor 372b, a third capacitor 372c, and a fourth capacitor 372d; and a diode 374. The impedance inverter circuit includes matching circuitry and an input balun. As shown, the input balun is a lattice balun that includes first inductor 370a, second inductor 370b, first capacitor 372a, and second capacitor 372b. In one example, diode 374 limits the direction of current flow to block RF receive signals from proceeding into decoupling bias branch (MC BIAS).

The pre-amplifier 362 may be a low input impedance pre-amplifier that is optimized for high source impedance by the impedance matching circuitry. The pre-amplifier may have a low noise reflection coefficient, y, and a low noise resistance, Rn. In one example, the pre-amplifier may have a source reflection coefficient of y substantially equal to 0.0 and a normalized noise resistance of Rn substantially equal to 0.0 in addition to the low noise figure. However, y values substantially equal to or less than 0.1 and Rn values substantially equal to or less than 0.2 are also contemplated. With the pre-amplifier having the appropriate y and Rn values, the pre-amplifier provides a blocking impedance for RF coil 301 while also providing a large noise circle in the context of a Smith Chart. As such, current in RF coil 301 is minimized, the pre-amplifier is effectively noise matched with RF coil 301 output impedance. Having a large noise circle, the pre-amplifier yields an effective signal to noise ratio (SNR) over a variety of RF coil impedances while producing a high blocking impedance to RF coil 301.

In some examples, the pre-amplifier 362 may include an impedance transformer that includes a capacitor and an inductor. The impedance transformer may be configured to alter the impedance of the pre-amplifier to effectively cancel out a reactance of the pre-amplifier, such as capacitance caused by a parasitic capacitance effect. Parasitic capacitance effects can be caused by, for example, a PCB layout of the pre-amplifier or by a gate of the pre-amplifier. Further, such reactance can often increase as the frequency increases. Advantageously, however, configuring the impedance transformer of the pre-amplifier to cancel, or at least minimize, reactance maintains a high impedance (i.e. a blocking impedance) to RF coil 301 and an effective SNR without having a substantial impact on the noise figure of the pre-amplifier. The lattice balun described above may be a non-limiting example of an impedance transformer.

In examples, the pre-amplifier described herein may a low input pre-amplifier. For example, in some embodiments, a "relatively low" input impedance of the preamplifier is less than approximately 5 ohms at resonance frequency. The coil impedance of the RF coil 301 may have any value, which may be dependent on coil loading, coil size, field strength, and/or the like. Examples of the coil impedance of the RF coil 301 include, but are not limited to, between approximately 2 ohms and approximately 10 ohms at 1.5 T magnetic field strength, and/or the like. The impedance inverter circuitry is configured to transform the coil impedance of the RF coil 301 into a relatively high source impedance. For example, in some embodiments, a "relatively high" source impedance is at least approximately 100 ohms and may be greater than 150 ohms.

The impedance transformer may also provide a blocking impedance to the RF coil 301. Transformation of the coil impedance of the RF coil 301 to a relative high source impedance may enable the impedance transformer to provide a higher blocking impedance to the RF coil 301.

Exemplary values for such higher blocking impedances include, for example, a blocking impedance of at least 500 ohms, and at least 1000 ohms.

Figure 3B:
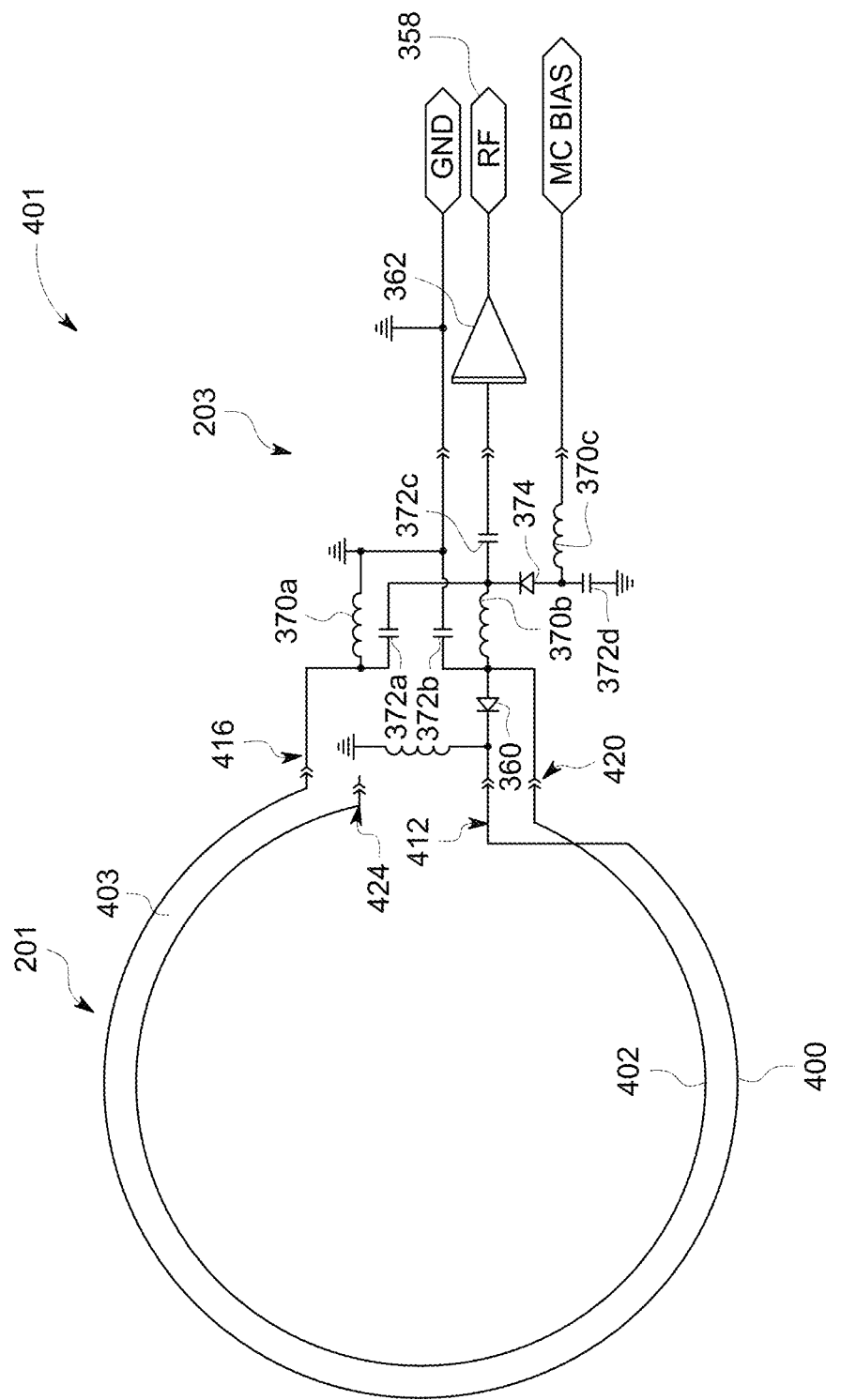
FIG. 3B is a schematic diagram of another exemplary RF coil shown in FIG. 2.

FIG. 3B is a schematic of an RF coil 401 and coupling electronics portion 203 according to another embodiment. The RF coil of FIG. 3B is a non-limiting example of the RF coil and coupling electronics of FIG. 2, and as such includes a coil loop 201 and coupling electronics portion 203. The coupling electronics allows the RF coil to transmit and/or receive RF signals when driven by the RF system 30 (shown in FIG. 1). The RF coil 401 includes a first conductor 400 in parallel with a second conductor 402. Different from the RF coil 301 shown in FIG. 3A that includes segmented conductors 300, 302, at least one of the first and second conductors 400, 402 are elongated and continuous.

In the illustrated embodiment, the first and second conductors 400, 402 are shaped into a coil loop that terminates to an interface. But in other embodiments, other shapes are possible. For example, the coil loop may be a polygon, shaped to conform the contours of a surface (e.g., housing), and/or the like. The coil loop defines a conductive pathway along the first and second conductors 400, 402. The first and second conductors 400, 402 are void of any discrete or lumped capacitive or inductive components along an entire length of the conductive pathway. The first and second conductors 400, 402 are uninterrupted and continuous along an entire length of the coil loop. The coil loop may also include loops of varying gauge of stranded or solid conductor wire, loops of varying diameters with varying lengths of the first and second conductors 400, 402, and/or loops of varying spacing between the first and second conductors. For example, each of the first and second conductors may have no cuts or gaps (no segmented conductors) or one or more cuts or gaps (segmented conductors) at various locations along the conductive pathway.

The first and second conductors 400, 402 have a distributed capacitance along the length of the coil loop (e.g., along the length of the first and second conductors 400, 402). The first and second conductors 400, 402 exhibit a substantially equal and uniform capacitance along the entire length of the coil loop. In the examples herein, the capacitance may grow in a uniform manner along the length of the first and second conductors 400, 402. At least one of the first and second conductors 400, 402 are elongated and continuous. In the illustrated embodiment, both the first and second conductors 400, 402 are elongated and continuous. But in other embodiments, only one of the first or second conductors 400, 402 may be elongated and continuous. The first and second conductors 400, 402 form continuous distributed capacitors. The capacitance grows at a substantially constant rate along the length of the conductors 400, 402. In the illustrated embodiment, the first and second conductors 400, 402 form elongated continuous conductors that exhibits DCAP along the length of the first and second conductors 400, 402. The first and second conductors 400, 402 are void of any discrete capacitive and inductive components along the entire length of the continuous conductors between terminating ends of the first and second conductors 400, 402. For example, the first and second conductors 400, 402 do not include any discrete capacitors, or any inductors along the length of the coil loop.

A dielectric material 403 separates the first and second conductors 400, 402. The dielectric material 403 may be selectively chosen to achieve a select distributive capacitance. The dielectric material 403 may be based on a desired permittivity E to vary the effective capacitance of the coil loop. For example, the dielectric material 403 may be air, rubber, plastic, or any other dielectric material. In one example, the dielectric material may be polytetrafluoroethylene (pTFE). For example, the dielectric material 403 may be an insulating material surrounding the parallel conductive elements of the first and second conductors 400, 402. Alternatively, the first and second conductors 400, 402 may be twisted upon one another to from a twisted pair cable. As another example, the dielectric material 403 may be a plastic material. The first and second conductors 400, 402 may form a coaxial structure in which the plastic dielectric material 403 separates the first and second conductors 400, 402. As another example, the first and second conductors 400, 402 may be configured as planar strips.

The first conductor 400 includes a first terminating end 412 and a second terminating end 416 that terminates at the interface. The first terminating end 412 is coupled to the coupling electronics portion 203. The first terminating end 412 may also be referred to herein as a "drive end." The second terminating end 416 is also referred to herein as a "second drive end."

The second conductor 402 includes a first terminating end 420 and a second terminating end 424 that terminates at the interface. The first terminating end 420 is coupled to the coupling electronics portion 203. The first terminating end 420 may also be referred to herein as a "drive end." The second terminating end 424 is also referred to herein as a "second drive end."

Figure 3C:
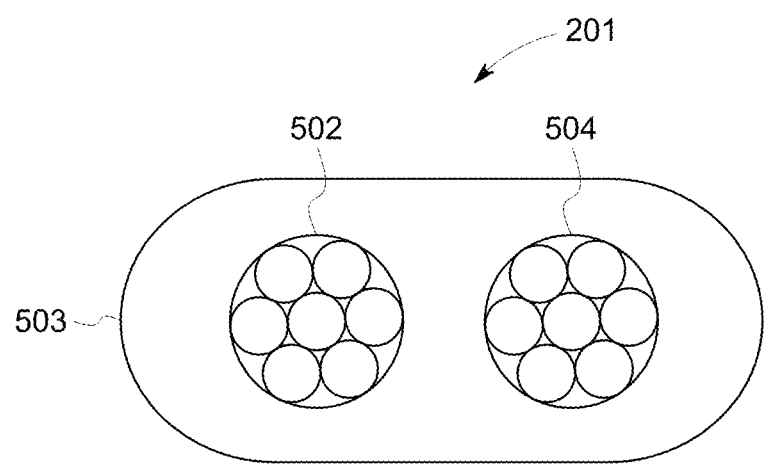
FIG. 3C is a cross-sectional view of an exemplary distributed capacitance coil loop of the RF coils shown in FIGS. 3A and 3B.

FIG. 3C shows a cross-sectional view of an exemplary coil loop 201. The coil loop 201 includes first wire conductor 502 and second wire conductor 504 surrounded by and encapsulated in dielectric material 503. The wire conductors 502, 504 may be the conductors 300, 302, 400, 402 described above. Each wire conductor may have a suitable cross-sectional shape, herein a circular cross-sectional shape. However, other cross-sectional shapes for the wire conductors are possible, such as elliptical, cylindrical, rectangular, triangular, hexagonal, etc. The wire conductors may be separated by a suitable distance, and the distance separating the conductors as well as the diameters of the wire conductors may be selected to achieve a desired capacitance. Further, each of the first wire conductor 502 and second wire conductor 504 may be a multi-strand wire conductor such as a seven conductor stranded wire (e.g., having seven stranded wires), but solid conductors may also be used instead of stranded wire. Stranded wire may provide more flexibility relative to solid conductors, at least in some examples.

As appreciated by FIGS. 3A and 3B, the two parallel conductors including the coil loop of an RF coil may each be continuous conductors, as illustrated in FIG. 3B, or one or both of the conductors may be non-continuous, as illustrated in FIG. 3A. For example, both conductors shown in FIG. 3A may include cuts, resulting in each conductor having two segments. The resulting space between conductor segments may be filled with the dielectric material that encapsulates and surrounds the conductors. The two cuts may be positioned at different locations, e.g., one cut at 135° and the other cut at 225° (relative to where the coil loop interfaces with the coupling electronics). By including discontinuous conductors, the resonance frequency of the coil may be adjusted relative to a coil that includes continuous conductors. In an example, an RF coil that includes two continuous parallel conductors encapsulated and separated by a dielectric, the resonance frequency may be a smaller, first resonance frequency. If that RF coil instead includes one discontinuous conductor (e.g., where one of the conductors is cut and filled with the dielectric material) and one continuous conductor, with all other parameters (e.g., conductor wire gauge, loop diameter, spacing between conductors, dielectric material) being the same, the resonance frequency of the RF coil may be a larger, second resonance frequency. In this way, parameters of the coil loop, including conductor wire gauge, loop diameter, spacing between conductors, dielectric material selection and/or thickness, and conductor segment number and lengths, may be adjusted to tune the RF coil to a desired resonance frequency.

Figure 4A:
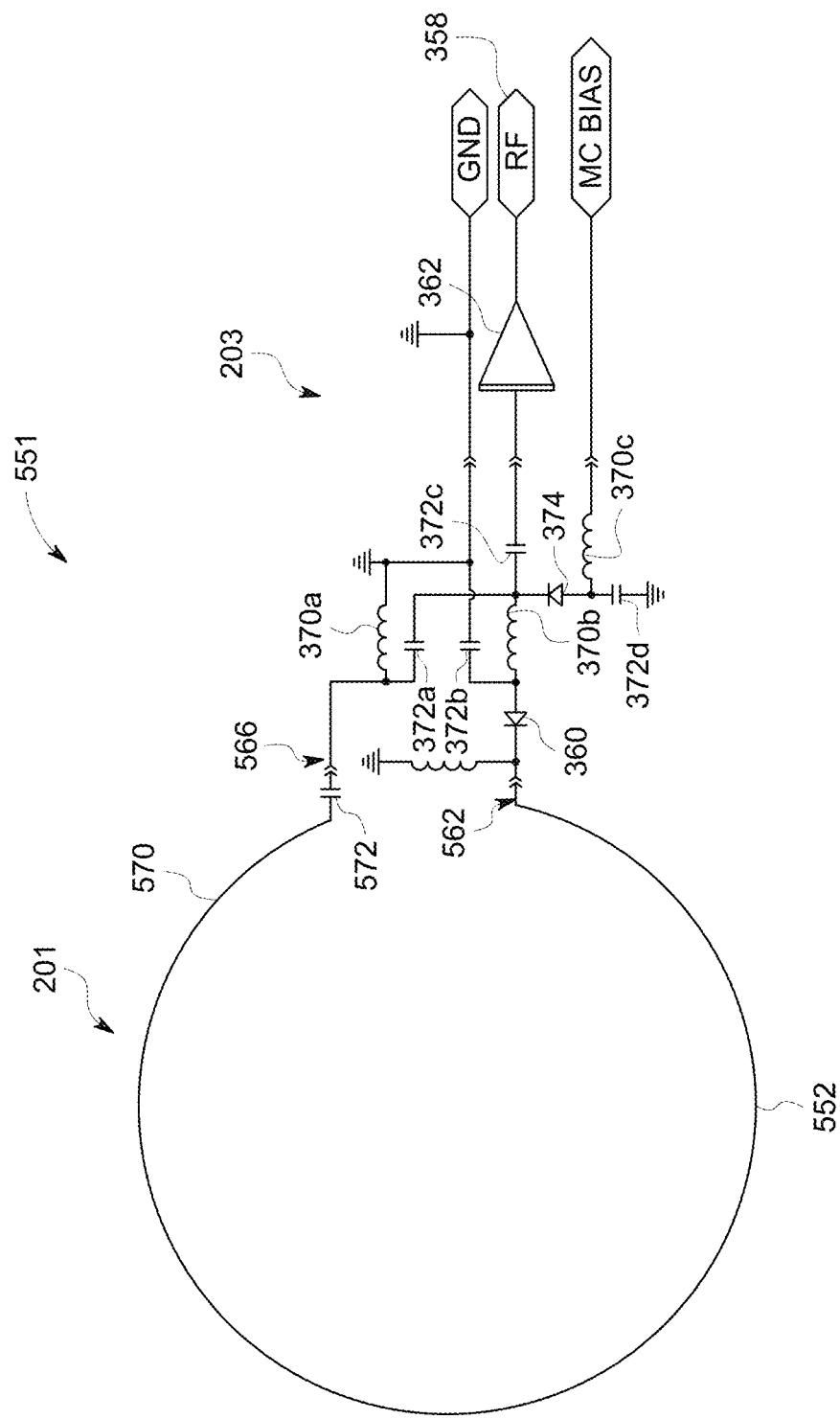
FIG. 4A is a schematic diagram of one more exemplary RF coil shown in FIG. 2.
Figure 4B:
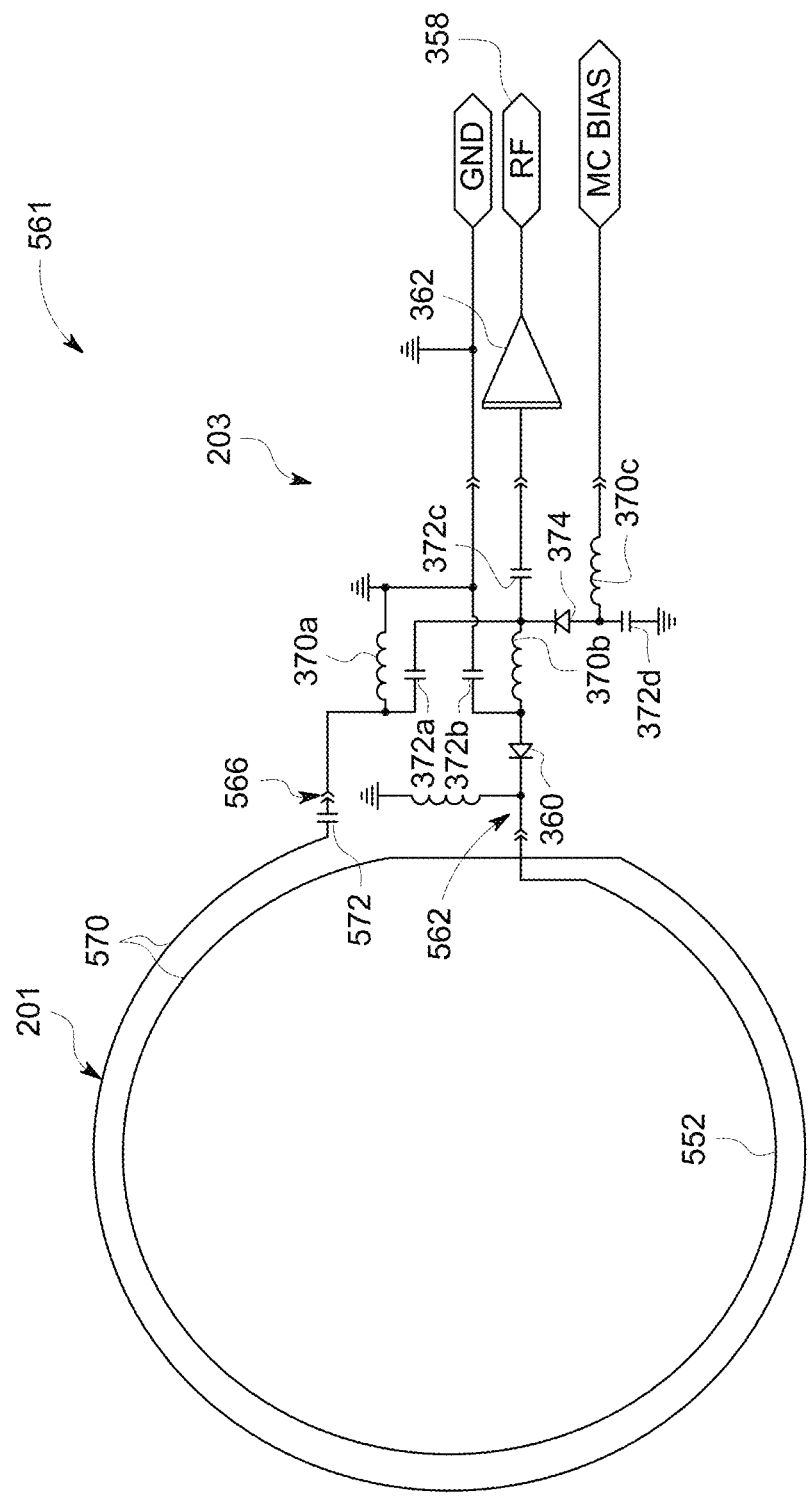
FIG. 4B is a schematic diagram of one more exemplary RF coil shown in FIG. 2.
Figure 4C:
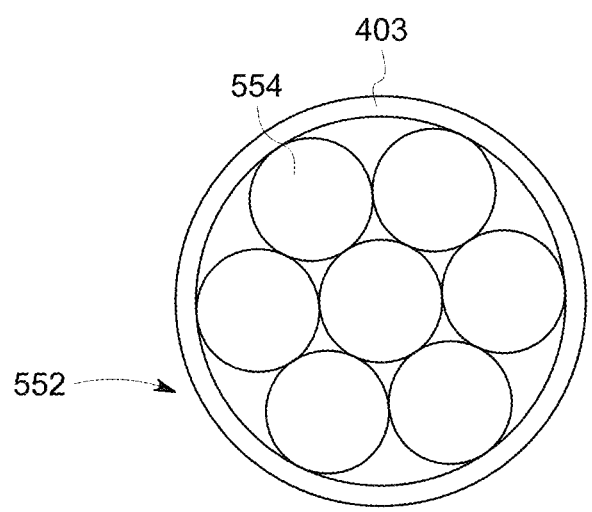
FIG. 4C is a cross-sectional view of an exemplary wire conductor used in the coil loop of the RF coils shown in FIGS. 4A and 4B

FIGS. 4A and 4B shows more exemplary RF coils 551, 561. FIG. 4C is a cross-sectional view of a wire conductor 552 used in the coil loop 201 of the RF coils 551, 561. Different from the coil loops 201 shown in FIGS. 3A-3C that include the first conductor 300, 400 and the second conductor 302, 402 and two driven ends at each end of the conductors, the coil loops 201 shown in FIGS. 4A-4B includes one single wire conductor 552 and one driven end 562, 566 at each end of the wire conductor 552. The coil loop 201 may form into one turn 570 (FIG. 4A) or a plurality of turns 570 (FIG. 4B). The resistance of the coil loop 201 increases approximately by the number of turns 570, and the loop loss increases approximately by square root of the number of turns 570, while the body loss increases approximately by the number of turns 570. As a result, the SNR of the coil loop 201 is increased approximately by the square root of the number of turns. In other words, multiple turns are used to increase the ratio of the body loss over the loop loss, compared with a single turn coil loop. The coil loop 201 forms into a shape of a circle, and may form into other shapes such as a polygon, oval, or irregular shapes. The coil loop 201 defines a conductive pathway along the wire conductor 552. The wire conductor 552 is shown as uninterrupted and continuous along an entire length of the coil loop. The coil loop may also include loops of varying gauge of stranded or solid conductor wire, loops of varying diameters with varying lengths of the conductors 552. For example, the conductor 552 may have no cuts or gaps (no segmented conductors) or one or more cuts or gaps (segmented conductors) at various locations along the conductive pathway. One or more capacitors 572 may be placed at the cuts, gaps, or at the end of the coil loop. The capacitance of the capacitors 572 may be variable.

FIG. 4C shows a cross-sectional view of the wire conductor 552. In the exemplary embodiment, the conductor 552 has a suitable cross-sectional shape, such as circular, elliptical, rectangular, triangular, or other shapes that enable the conductor 552 functions as described herein. The insulating material 403 surrounds the conductors 552. The dielectric material 403 may be rubber, plastic, or any other dielectric material. The conductor 552 includes one or a plurality of strands 554. For example, the conductor 552 is a single-strand wire conductor. Alternatively, the conductor 552 is a multi-strand wire conductor having a plurality of strands 554, where an individual strand 554 may be surrounded by insulating material or not surrounded by insulating material. The individual strands 554 may be twisted upon each other or may be parallel to each other, along the length of the strand 554.

Referring back to FIGS. 2, 3A, 3B, 4A, and 4B, the coil loop 201 is coupled to coupling electronics portion 203. The coupling electronics portion 203 may be the same coupling electronics described above with respect to FIGS. 2, 3A, 3B, 4A, and 4B, and hence like reference numbers are given to like components and further description is dispensed with.

The RF coils presented above with respect to FIGS. 2, 3A, 3B, 4A, and 4B may be used in order to receive MR signals during an MR imaging session. As such, the RF coils of FIGS. 2, 3A, 3B, 4A, and 4B are configured to be coupled to a downstream component of the MR system 10. The RF coils of FIGS. 2, 3A, 3B, 4A, and 4B may be present in an array of RF coils having various configurations.

Figure 5:
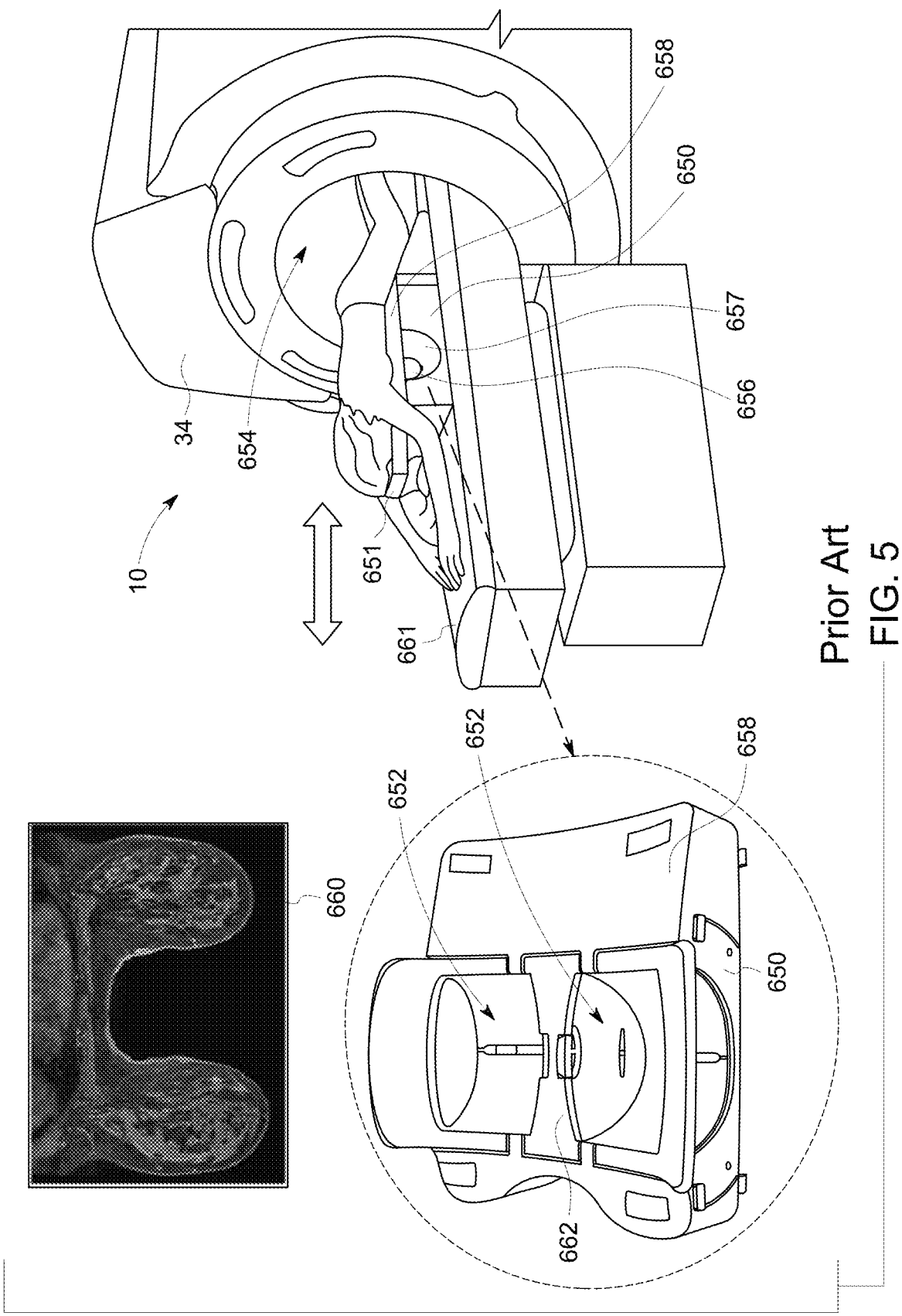
FIG. 5 shows breast imaging conducted with a known breast RF coil.
Figure 6A:
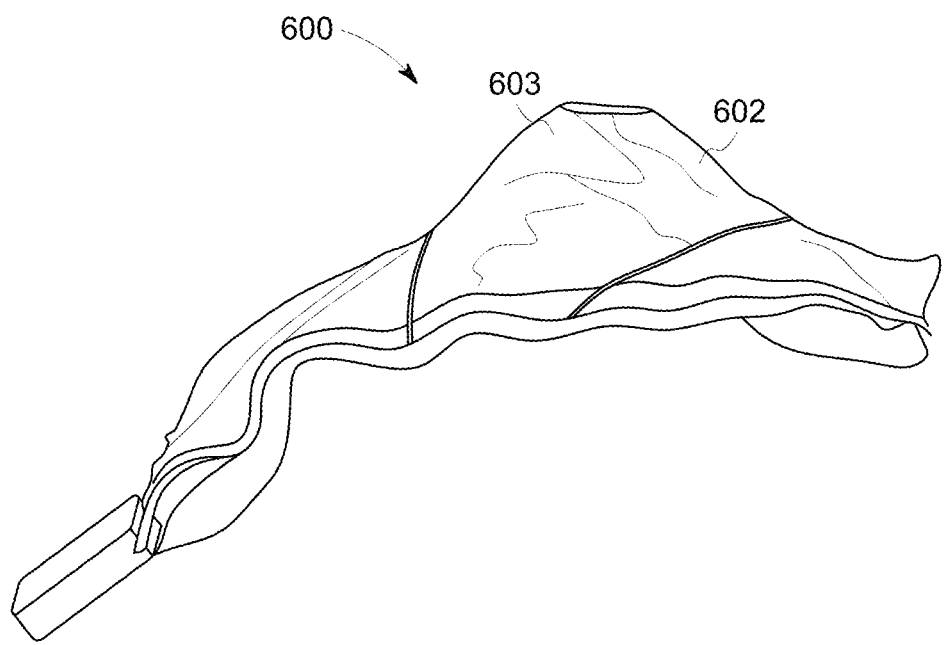
FIG. 6A is a left perspective view of an exemplary RF coil assembly.
Figure 6B:
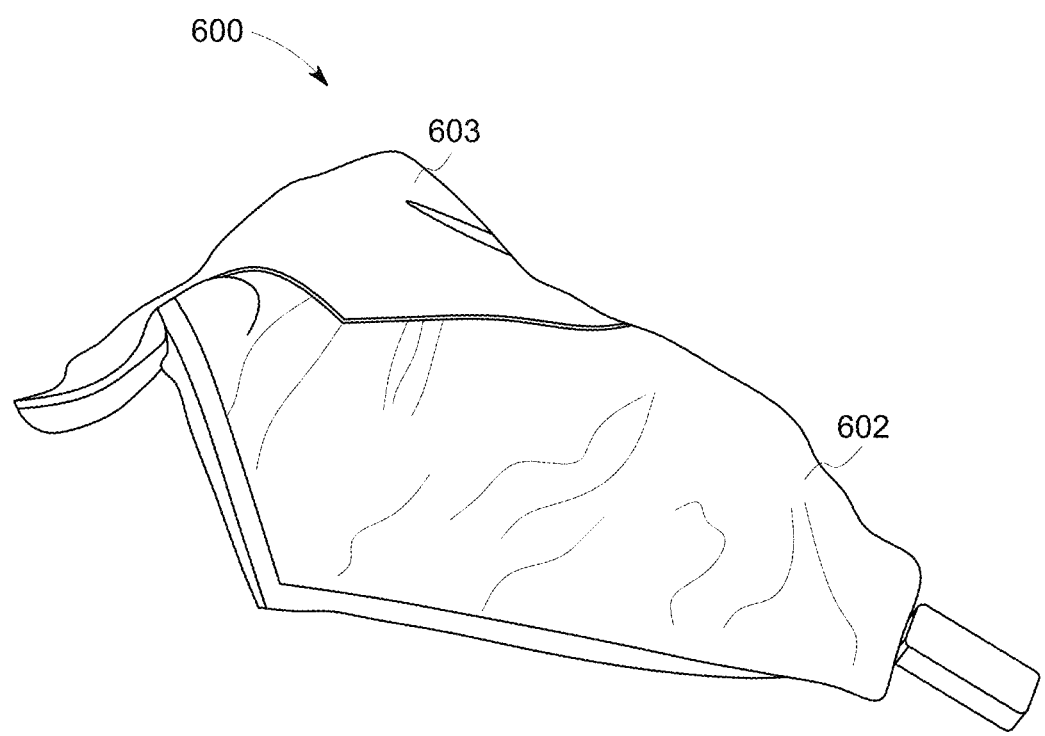
FIG. 6B is a right perspective view of the RF coil assembly shown in FIG. 6A.
Figure 6C:
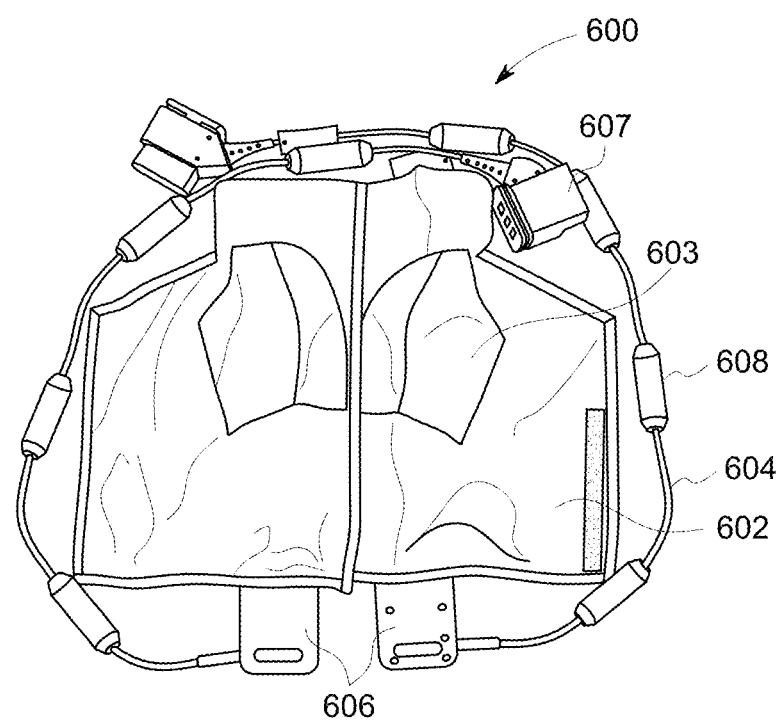
FIG. 6C is a front view of the RF coil assembly shown in FIG. 6A.
Figure 6D:
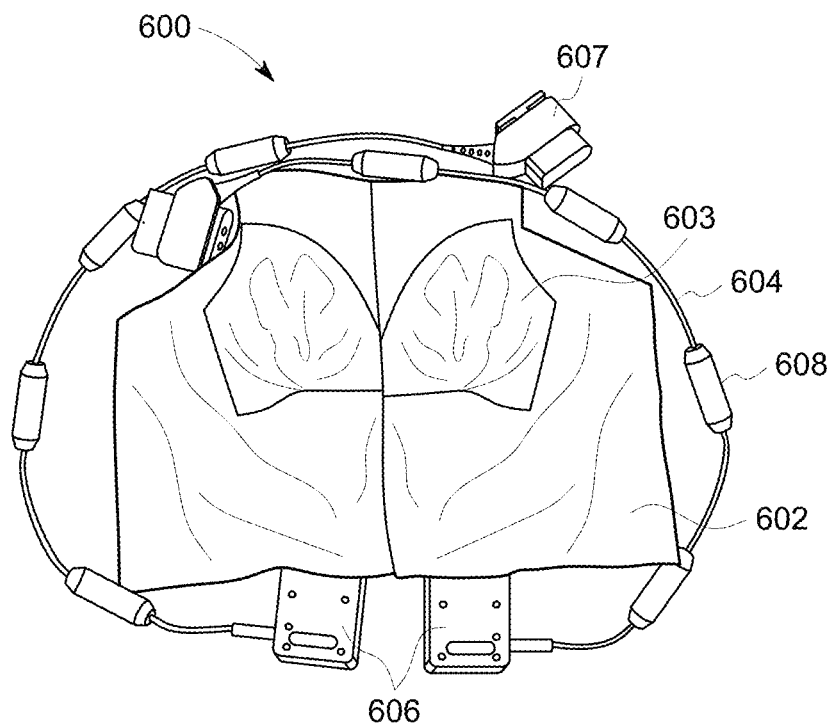
FIG. 6D is a rear view of the RF coil assembly shown in FIG. 6A.
Figure 6E:
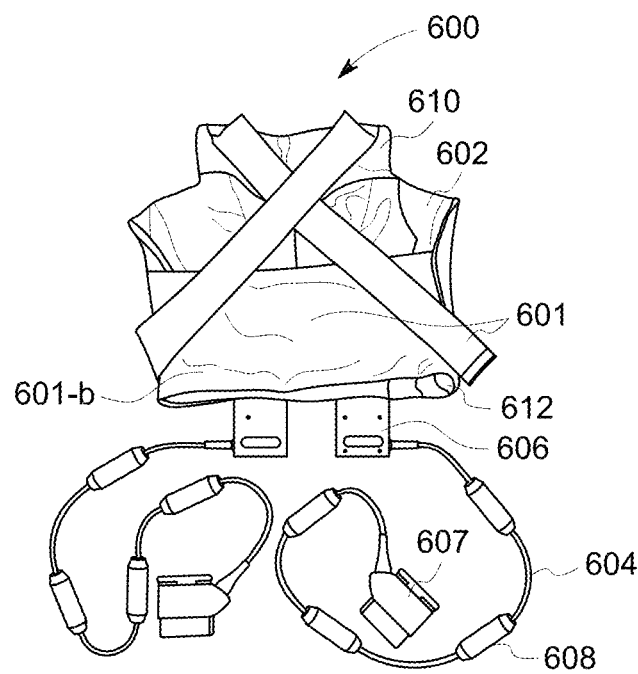
FIG. 6E is a rear view of another exemplary RF coil assembly.

FIGS. 5-6E show a conventional breast RF coil 650 (FIG. 5) and an exemplary RF coil assembly 600 (FIGS. 6A-6E). FIG. 6A is a left perspective view of the RF coil assembly 600. FIG. 6B is a right perspective view of the RF coil assembly 600. FIG. 6C is the front view of the RF coil assembly 600. FIG. 6D is the rear view of the RF coil assembly 600. FIG. 6E shows the RF coil assembly 600 having add-on straps 601.

FIG. 5 shows the conventional breast RF coil 650, a subject lying prone over the conventional breast RF coil 650, with the subject's head resting on a head rest 651, and an image 660 acquired with the conventional breast RF coil 650. The breast RF coil 650 forms into two cavities 652 sized to receive the breasts 656 of the subject. Because the breast RF coil 650 is heavy and rigid, for the subject's comfort, breast imaging is performed while the subject lies prone in the bore 654 of the magnet assembly 34. A scan session of MR imaging takes approximately one to two hours. Lying prone for that long is uncomfortable, and becomes difficult for those with musculoskeletal weakness or advanced age. The breast RF coil 650 encompasses the breasts 656. The areas below the armpit and upper chest areas, such as level III axillary lymph nodes and supraclavicular lymph nodes, which are important for diagnostic and treatment purposes, however, are usually not encompassed by the breast RF coil 650, as shown in the image 660.

Because the breast RF coil 650 is rigid and the sizes of the cavities 652 are fixed, the breast RF coil 650 cannot accommodate subjects who have large-sized breasts 656. On the other hand, for subjects who have relatively small-sized breasts 656, the breast RF coil 650 is not proximate the breasts 656 and the SNR of acquired signals is less than that of signals acquired with the breast RF coil 650 being proximate to the breast.

During biopsy, to replicate the locations of the tissue between imaging and biopsy, MR biopsy is performed prone because MR breast imaging is typically performed prone and the breast shapes and tissue locations would change when the subject changes from lying prone to supine. The breast RF coil 650 provides limited access for the breast, with only a side access 657 to the breast 656. To access the inner breast, the biopsy needle has to pass through an entire section of the breast, causing unnecessary damage to the tissue of the subject.

In addition, because the breast RF coil 650 is designed to include cavities for receiving breasts 656, a platform 658 on which the chest area of the subject lie is raised above the table 661 of the MR system 10, which reduces the available bore space by an amount such as 15-18 centimeter (cm) (6-7 inches (in.)) in height, therefore restricting the access of MR breast scan for some subjects.

Medical images may also be used for surgery planning. Breast surgery, however, is performed supine to access the breast tissue. With the conventional breast RF coil 650, MR breast images are not helpful in surgery planning because the conventional breast RF coil 650 usually acquires prone images in practice.

In contrast, the RF coil assembly 600 described herein allows supine and prone breast imaging, and covers other area of the subject's torso, besides the breasts 656.

In the exemplary embodiment, the RF coil assembly 600 includes an outer enclosure 602 and a plurality of RF coils 702 (see FIGS. 7A-7G described later). The RF coils 702 are enclosed inside the outer enclosure 602. The RF coil assembly 600 also includes contoured sections 603. The contoured sections 603 are sized to receive a curved anatomy of the subject, such as a breast of the subject.

The outer enclosure 602 may be fabricated from a polyurethane fabric such as DARTEX®. The material for the outer enclosure 602 may be waterproof, semi-vapor permeable, and anti-fungal treated. The material may be "fabric weldable" or sealed by RF welding to create welded seams and a waterproof finish suited for medical applications and environments. The material allows for ease of cleaning, and protects the internal electronics from getting wet or soiled. Further, the material is biocompatible and does not irritate the skin of a human subject, and therefore suitable for medical uses. The material is also lighted weighted and flexible. Underneath the outer enclosure 602, the RF coil assembly 600 may include an inner enclosure (not shown). The inner enclosure covers the RF coils 702. The inner enclosure may be fabricated from a material that provides padding, spacing, and/or flame-retardant properties, such as NOMEX®.

In the exemplary embodiment, the RF coil assembly 600 further includes an RF coil array interfacing cable 604 (FIGS. 6C-6E) extending from a coil interfacing connector 606 of the RF coil array 700 (see FIGS. 7A-7G described later). The RF coil array interfacing cable 604 may be used to connect the RF coil assembly 600 to other components of the MR system 10 such as the RF system 30 through a coil array interfacing connector 607. The RF coil array interfacing cable 604 may include a plurality of baluns 608 or contiguous/continuous distributed baluns (not shown).

In some embodiments, the RF coil assembly 600 further includes straps 601 (FIG. 6E). The straps 601 may be attached to the enclosure 602 of the RF coil assembly 600 through a fastener, such as hook-and-loop fasteners, clips, or buttons. The straps 601 are used for adjusting the fitting of the RF coil assembly 600 onto the subject. The straps 601 may be a back strap 601-b that wraps around the subject's back. The strap 601 may be used to form a loop around the subject, adjusting the fit of the RF coil assembly 600 to the anatomy of the subject. For example, the strap 601 may be attached to the shoulder portion 610 of the outer enclosure 602 at one end and diagonally to the lower portion 612 of the outer enclosure 602 at the other end. As a result, the scan setup time with the RF coil assembly 600 is reduced because the subject may directly adjust the fitting of the RF coil assembly 600 onto the imaged anatomy, instead of relying on a technologist when a conventional breast RF coil 650 is used.

In some embodiments, the RF coil assembly 600 may be formed into a vest such that the RF coils 702 are in the front section and a back section coupled to the front (see FIGS. 7A and 7C described later). The back section may be formed as one piece with the front section, or as a separate piece and attached with the front with fasteners such as hook-and-loop fasteners, clips, or buttons.

Figure 7A:
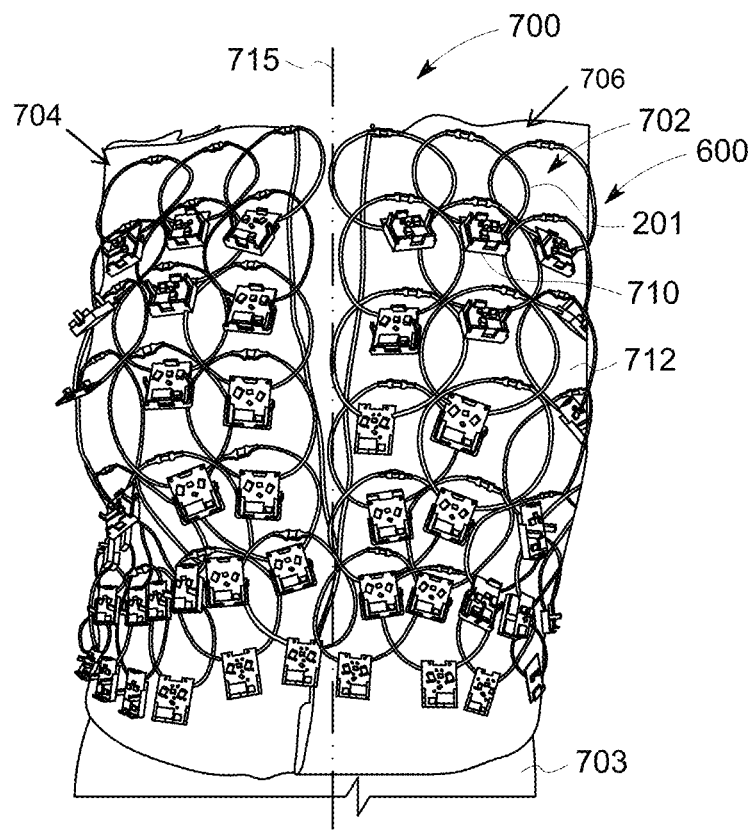
FIG. 7A is a front view of the RF coil assembly shown in FIG. 6B, with the enclosure of the RF coil assembly removed.
Figure 7B:
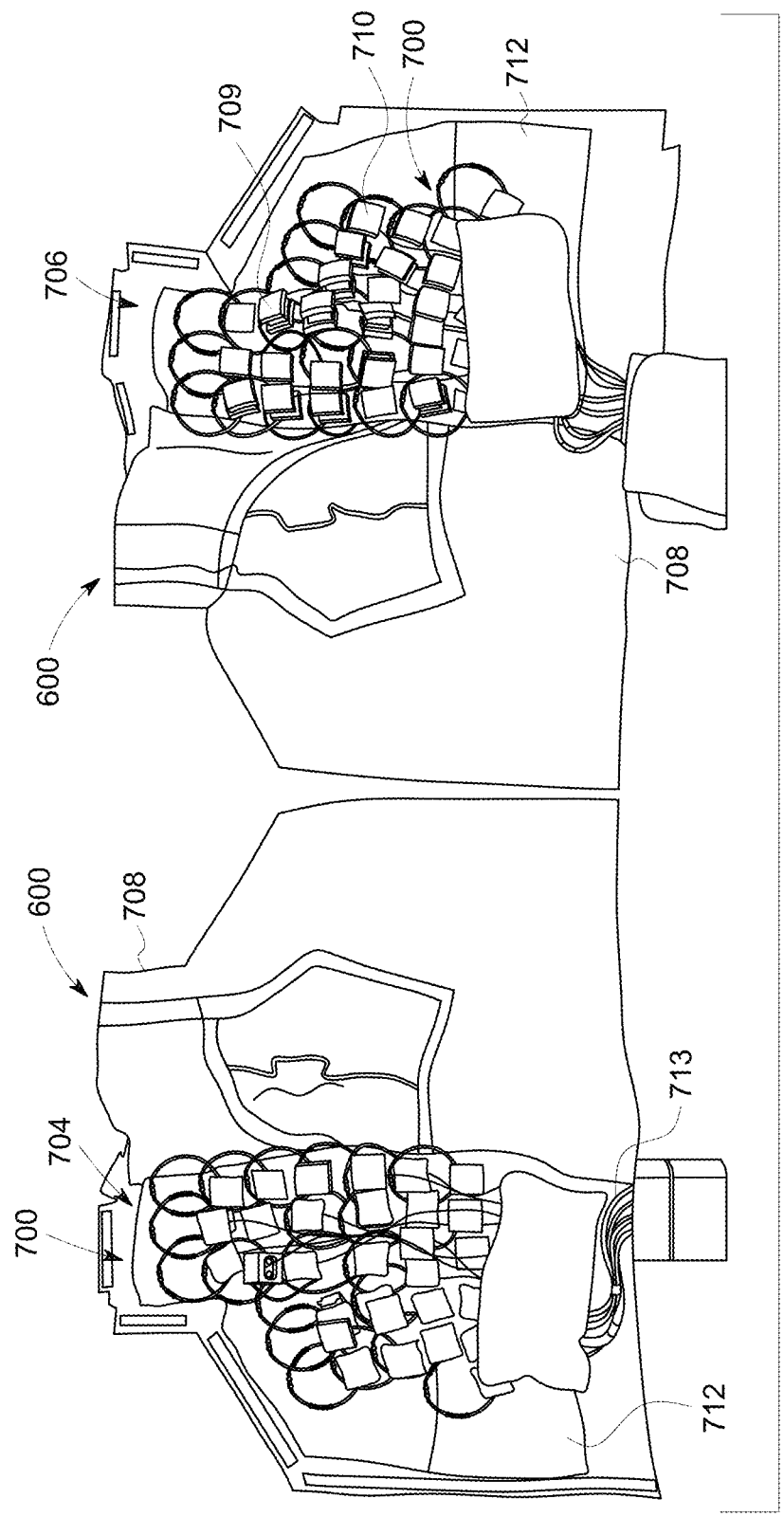
FIG. 7B shows sections of the RF coil assembly shown in FIG. 7A.

FIGS. 7A-7G show an exemplary RF coil array 700 of the RF coil assembly 600. FIG. 7A is a front view of the RF coil assembly 600 donned on a mannequin 703 with the outer enclosure 602 and inner enclosure, if any, removed. FIG. 7B shows front views of the left section 704 and the right section 706 of the RF coil assembly 600, with a cover 708 separated away from the RF coil array 700. The left section 704 and the right section 706 are referred herein as in FIGS. 7A-7G, not the subject's left or right because the left section 704 would be on the subject's right and the right section 706 would be on the subject's left. To assemble the RF coil assembly 600, the cover 708 may be placed over the RF coil array 700, an inner enclosure if used is placed over the cover, and the outer enclosure 602 is placed over the inner enclosure or over the cover 708 if an inner enclosure is not used. Different from the RF coil assembly shown in FIG. 7A, the coupling electronics portions 710 of the RF coil array 700 are covered with a padding material 709.

Figure 7C:
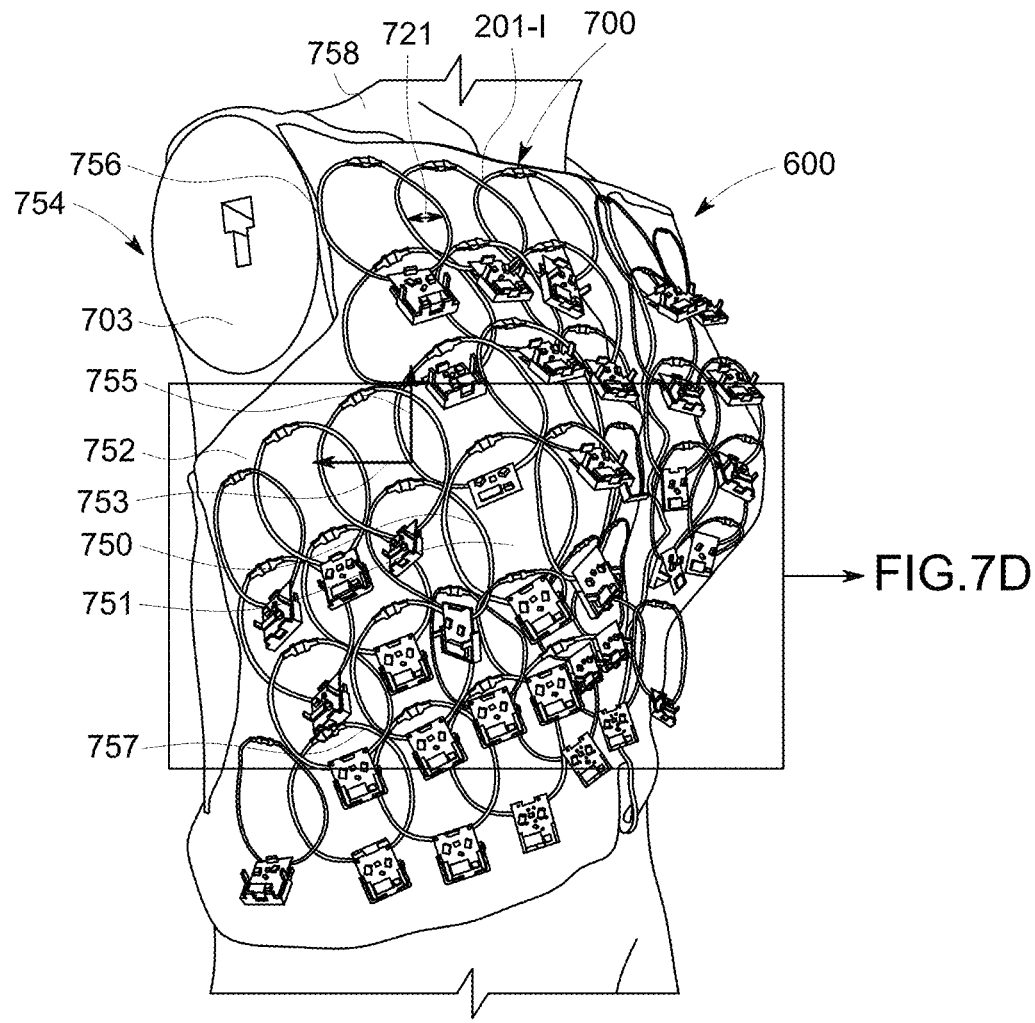
FIG. 7C is a perspective view of the RF coil assembly shown in FIG. 7A.
Figure 7D:
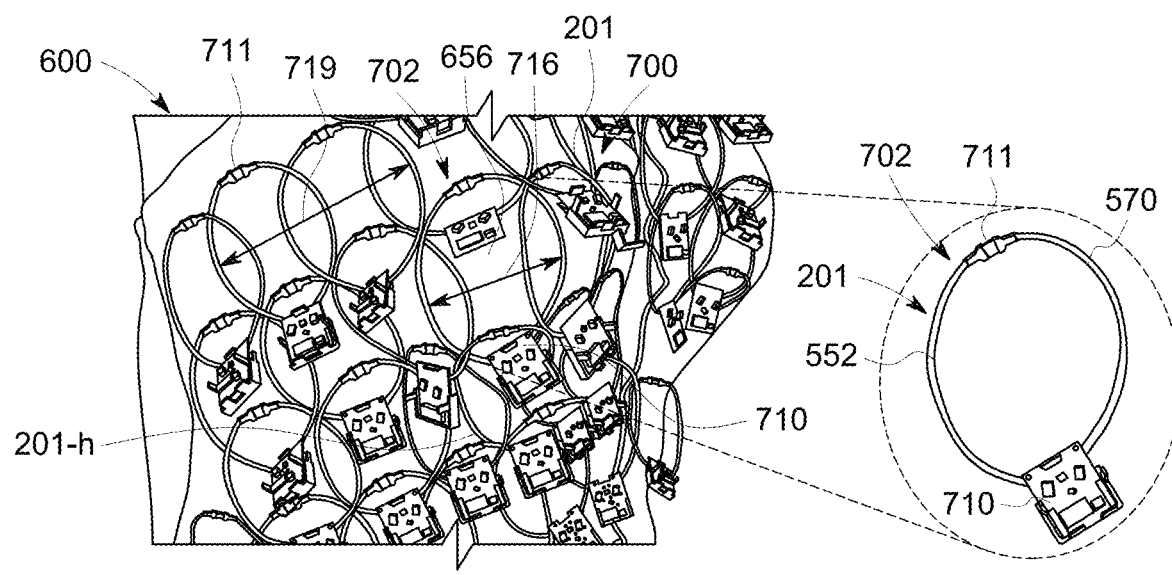
FIG. 7D is a partial view of the RF coil assembly shown in FIG. 7C.
Figure 7E:
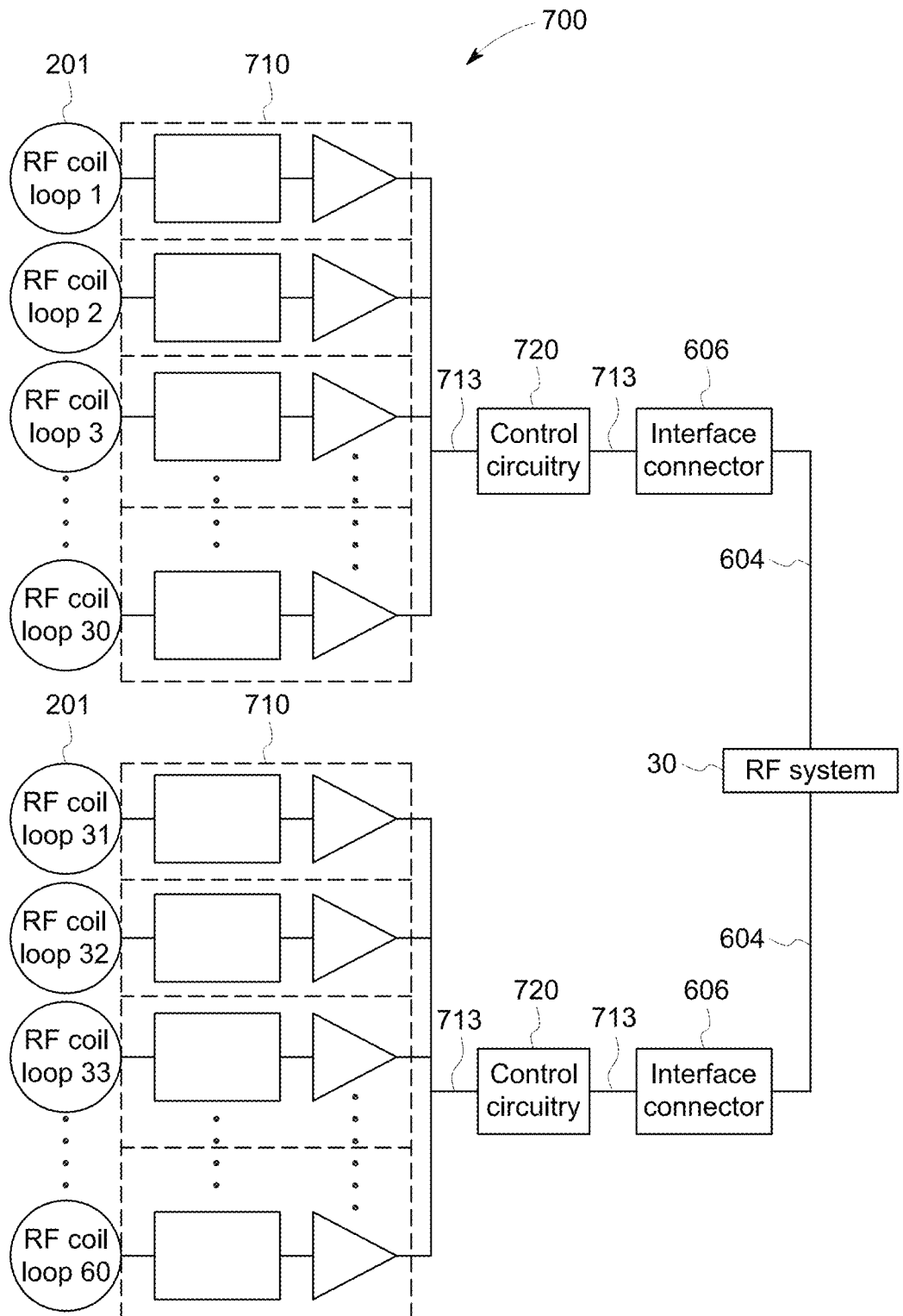
FIG. 7E is a block diagram of the RF coil assembly shown in FIG. 7A.
Figure 7F:
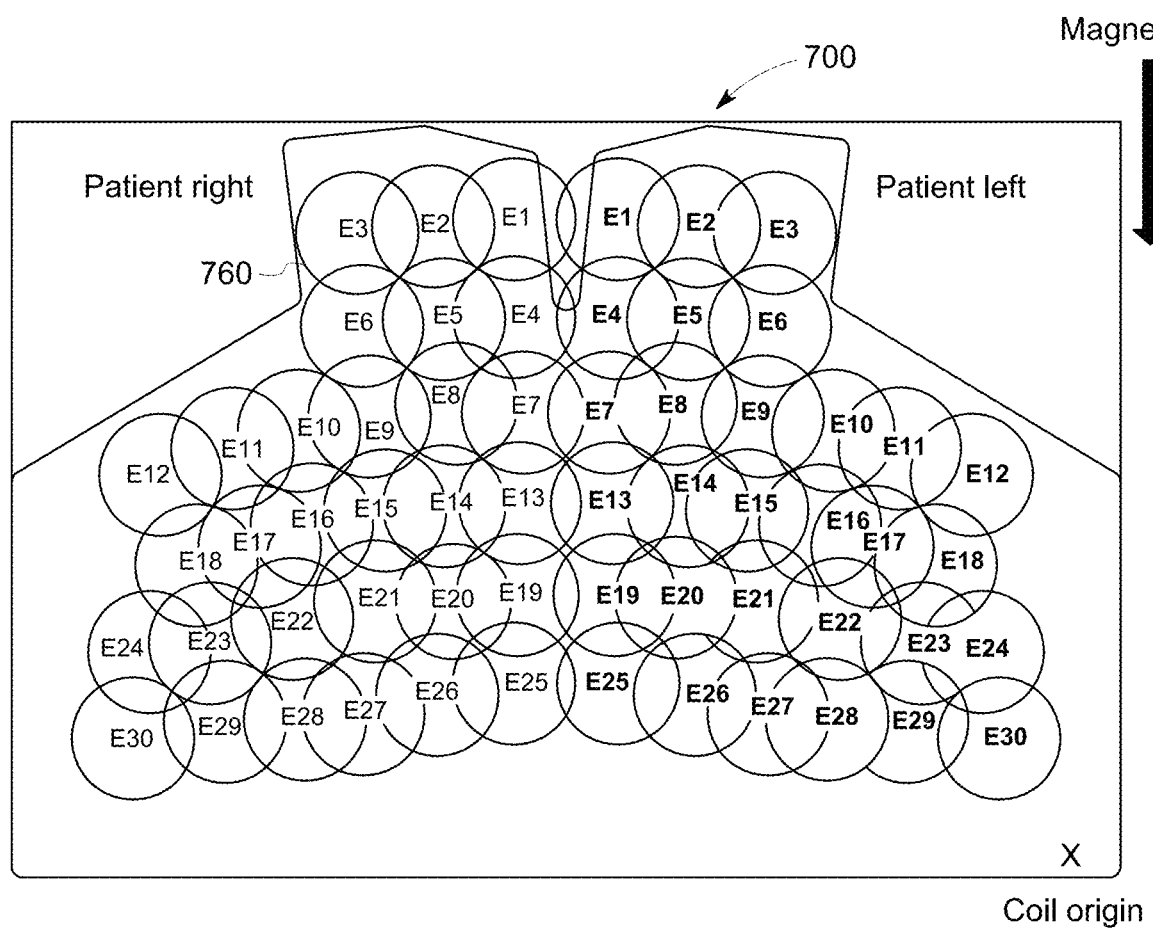
FIG. 7F is a schematic diagram showing the layout of RF coil loops in the RF coil assembly shown in FIG. 7A.
Figure 7G:
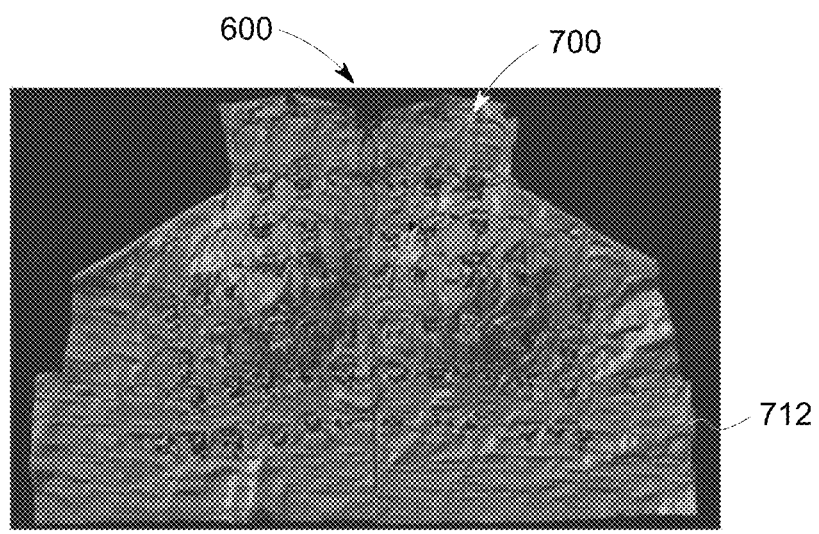
FIG. 7G shows the layout of the RF coil loops of the RF coil assembly shown in FIG. 7A.

FIG. 7C is a perspective view of the RF coil array 700 shown in FIG. 7A. FIG. 7D shows a contoured region of the RF coil array 700 shown in FIG. 7C and an RF coil 702 by itself. FIG. 7E is a block diagram of the RF coil array 700. FIG. 7F is a schematic diagram of the layout of coil loops 201 of the RF coil array 700. FIG. 7G is an optical image of the RF coil assembly 600 including only the RF coils 702 and a lining 712.

In the exemplary embodiment, the RF coil assembly 600 includes the RF coil array 700 overlaid over the lining 712. The lining 712 includes a contoured portion 751 (FIG. 7C). The lining 712 is fabricated from a flexible support material, such as Norfab cloth. Each RF coil loop 201 of the RF coil array 700 is coupled to the lining 712, via stitching or other attachment mechanisms.

In the exemplary embodiment, the RF coil array 700 includes a plurality of RF coils 702. The RF coils 702 may be the RF coil 202, 301, 401, 551, 561 described above. The RF coil 702 includes the RF coil loop 201 and the coupling electronics portion 710. The coupling electronics portion 710 includes the coupling electronics portion 203 described above.

In the depicted embodiment, the RF coil loop 201 includes multi-strand wire conductor 552. In one example, the wire conductor 552 includes 19 strands that are 36 AWG each for an overall thickness of 24 AWG, and the cross section of the wire conductor 552 has a diameter of 0.025 inches (0.06 cm). A coil loop 201 including multi-strand conductors 552 has a higher penetration depth and a higher SNR than a coil loop 201 of the same diameter that includes distributed capacitance wire conductors 300, 302, 400, 402. Therefore, the size of the coil loop 201 may be reduced by including multi-strand wire conductors 552 instead of distributed capacitance wire conductors 300, 302, 400, 402 for the same penetration depth, and consequently an increase number of RF coils 702 may be included in the coil array 700. The wire conductor 552 may be segmented at the location opposite the coupling electronics portion 710, with the segments electrically coupled to each other through a capacitor 711. The capacitor 711 may include a fixed valued capacitor and a variable capacitor electrically connected in parallel to each other. The capacitance of the coil loop 201 may be adjusted by adjusting the capacitance of the capacitor 711. The capacitor 711 may be formed into a PCB. The capacitor 711 may be soldered with the wire conductor 552. Alternatively, the coil loop 201 does not include the capacitor 711. In some embodiments, the wire conductor 552 is a single-strand wire conductor.

In the depicted embodiment, the wire conductor 552 forms into one turn 570 (FIG. 7D). In some embodiments, the wire conductor 552 forms into a plurality of the turns 570 (see FIG. 4B). In other embodiments, the RF coil loop 201 includes a distributed capacitance coil loop formed by distributed capacitance wire conductors 300, 302, 400, 402 and does not include the capacitor 711.

In the exemplary embodiment, the circular coil loop 201 is depicted as an example only. The coil loop 201 may in other shapes, such as oval, irregularly curved, or rectangular, that enable the coil loop 201 to function as described herein. In one example, the coil loop 201 is fabricated from a flexible 1.3 millimeter (mm) diameter conductor optimized for zero reactance at 127.73 MHz, the resonance frequency of a 3T MR system. The RF coils 702 may be designed for an MR system 10 having a different field strength, such as 1.5 T. Because the wire conductor 300, 302, 400, 402, 552 of the coil loop 201 is flexible, the shape of the coil loop 201 may change and be deformed to conform to a curved anatomy of the subject, such as deforming from being circular to other shapes such as oval, elliptical, or irregular shapes like Pringles® chips. A coil-interfacing cable 713 (FIGS. 7B and 7E) is connected to and extends from each coupling electronic PCB or coupling electronics portion 710 to the coil interfacing connector 606. The coil interfacing connector 606 further couples to other components of the MR system 10 such as the RF system 30 through the coil array interfacing cable 604 (FIG. 7E, also see FIGS. 6C-6E). For example, the coil interfacing connector 606 is coupled to the coil array interfacing connector 607 (see FIGS. 6C-6E) and the coil array interfacing connector 607 is plugged in a coil interface when the RF coil assembly 600 is in use, coupling the RF coil assembly 600 to the rest of the MR system 10, such as the RF system 30.

The coupling electronics portion 710 may include a decoupling circuit, impedance inverter circuit, and a pre-amplifier. The decoupling circuit may effectively decouple an RF coil during a transmit operation. The impedance inverter circuit may form an impedance matching network between an RF coil and the pre-amplifier. The impedance inverter circuit is configured to transform a coil impedance of a RF coil into an optimal source impedance for the pre-amplifier. The impedance inverter circuit may include an impedance matching network and an input balun. The pre-amplifier receives MR signals from a RF coil and amplifies the received MR signals. In one example, the pre-amplifier may have a low input impedance that is configured to accommodate a relatively high blocking or source impedance. The coupling electronics portion 710 may be packaged in a small PCB, for example having an area of approximately 2 cm$^2$ or smaller. The PCB may be protected with the pad or padding material 709 (see FIG. 7B), a conformal coating, or an encapsulating resin.

Control circuitry 720 (FIG. 7E) is the MC BIAS for switching RF coils between receive and decoupled modes. Elements of the control circuitry 720 are incorporated in both the coupling electronics portion 710 and the coil interfacing connector 606.

In the exemplary embodiment, the RF coil assembly 600 includes two RF coil arrays 700. The two RF coil arrays 700 are separable from each other. The two RF coil arrays 700 are both configured to be electrically coupled to the RF system 30.

In the exemplary embodiment, the RF coil array 700 includes a contoured portion 750 (FIG. 7C). The contoured portion 750 is configured to conform to a curved anatomy of the subject, such as breasts. The contoured portion 750 covers and conforms to the contoured portion 751 of the lining 712. The RF coil array 700 may include an armpit portion 752. The armpit portion 752 is positioned sideways away from the contoured portion 750 in a first direction 753. In some embodiments, the RF coil assembly 600 forms an armpit hole 754 sized for arms of the subject to extend through. The armpit portion 752 is positioned adjacent the armpit hole 754. The armpit portion 752 is configured to cover the area around the armpit. The RF coil array 700 may further include an upper chest portion 756 positioned away from the contoured portion 750 in a second direction 755 that is substantially perpendicular to the direction of the armpit portion 752. The upper chest portion 756 is configured to cover an upper chest area of the subject. In some embodiments, the RF coil assembly 600 may form a neck hole 758. The upper chest portion 756 is positioned adjacent the neck hole 758. An RF coil array 700 having the armpit portion 752 and/or the upper chest portion 756 is advantageous because the RF coil assembly 600 covers lymph nodes under the subject's arm or on the upper chest such as level III axillary lymph nodes below the armpit and supraclavicular lymph nodes on the upper chest, which are not covered by a conventional breast RF coil 650. Moreover, the RF coil assembly 600 further includes a lower torso portion 757 positioned away from the contoured portion 750 in a direction opposite to the second direction 755. The lower torso portion 757 is configured to cover the lower chest area, the abdominal area, and/or the waist area of the subject, allowing scanning of the entire torso of the subject. That is, the RF coil assembly 600 may be configured as a torso RF coil assembly.

In the depicted embodiment, the RF coil array 700 is a 60-channel RF coil array. 60-channel means that there are 60 RF coils 702, each having the RF coil loop 201 coupled with the coupling electronics portion 710. The RF coils 702 are in multiple rows, for example six rows of RF coils 702 (FIGS. 7A, 7C, and 7F). Each row 760 (FIG. 7F) includes one or more RF coils 702. For example, the first and second rows have six RF coils 702, while the third to sixth rows have twelve RF coils 702. In one example, the RF coil loop 201 has a diameter 716 (FIG. 7D) of 7 cm. As used herein, the size of the RF coil loop 201 is the diameter 716 of the RF coil loop 201. If the RF coil loop 201 is in a shape other than circular, the size of the RF coil loop 201 is the dimensions of the RF coil loop 201, such as the length or width of the RF coil loop 201. A smaller sized RF coil loop, e.g., 5 cm in diameter, may be used to conform to a curved anatomy having a greater curvature, as well as increasing the acceleration factor because more coils may be included to cover the same area of the curved surface.

The spacing 719 (FIG. 7D) between adjacent coil loops may be the same or may be different. For example, RF coil loops 201-h (FIG. 7D) are more overlapped with one another than RF coil loops 201-1 (FIG. 7C) with one another. When two RF coil loops 201 do not overlap with one another, current fed into one RF coil loop 201 induces current in another RF coil loop 201, which is referred to as mutual inductance coupling between the coil loops. The coupling electronics portion 710 is used to reduce the coupling. The mutual inductance coupling is also reduced by overlapping the RF coil loops 201. When one RF coil loop 201 overlaps with another RF coil loop 201 by approximately 25%, where the overlapped distance 721 (FIG. 7C) between the two RF coil loops is approximately 25% of the diameter of the RF coil loop 201, the two RF coil loops 201 are critically overlapped, where the mutual inductance coupling is zero. If the RF coil loops 201 overlap 25% or more, the RF coil loops 201 are highly overlapped. Although the mutual inductance coupling is not minimized when the RF coil loops 201 are overlapped more than 25%, the coupling is reduced by the coupling electronics portion 710. Highly overlapped RF coil loops 201 allow more coil loops 201 in one area and higher acceleration factor in the image acquisition, as well as better conforming to a contoured anatomy, such as breasts. For example, the RF coil loops 201-h positioned along the curves of the breasts 656, e.g., the RF coil loops 201-h in the contoured portion 750, overlap more than 30% and are more overlapped than the RF coil loops 201-1 positioned at less curved areas such as the upper chest area and the waist area, for example, the RF coil loops 201-1 in the armpit portion 752 or the upper chest portion 756. Another advantage of highly overlapped RF coil loops 201 is that an increased sized RF coil loop may be used to conform to the curvature. An RF coil 201 of an increased size has increased tissue penetration, thereby increasing the tissue coverage and SNR.

The RF coil assembly 600 are shown having two sections, left and right sections 704, 706 separable along a longitudinal midline 715 (FIG. 7A), which aligns with the sternum of the subject when the RF coil assembly 600 is placed over the subject. The lining 712 is also separable along the longitudinal midline 715. Alternatively, the RF coil assembly 600 may be configured as one RF coil array 700. Further, only one of the two sections 704, 706 may be used during scanning. That is, bilateral or unilateral breast imaging is available with the RF coil assembly 600. For example, if only the left breast of the subject has tumor and only the left side of the body will be imaged such as for biopsy purposes, only the left section 704 of the RF coil assembly 600 is used during the scanning. Alternatively, both the left and right sections 704, 706 are used for imaging both sides of the body of the subject, where images or image sections of the healthy side may be used for comparison purposes.

The RF coil assembly 600 is flexible and conforms to the curved anatomy of the subject. Therefore, the RF coil assembly 600 accommodates subjects of various chest sizes and having various sizes of breasts. Further, because the subject lies supine in the bore 654 of the magnet assembly 34 (FIG. 5), the available bore space is greatly increased, compared to the conventional breast RF coil 650, further increasing the availability of breast imaging to subjects.

The RF coil assembly 600 is advantageous also over an RF coil assembly having RF coil loops placed on a sheet of flexible material, which is referred to as a blanket flexible RF coil assembly. A sheet of flexible material may be fitted over a curved object in one dimension, but not in two dimensions. That is, a sheet of flexible material cannot be fit over a curved object without introducing folded areas or wrinkles. For example, a sheet of paper would be not be able to fit over a person's head without introducing folds or wrinkles. As a result, some RF coil loops of the blanket flexible RF coil assembly may conform to part of the curvature of the curved object, but other RF coil loops of the blanket flexible RF coil assembly are either at a distance from the object, which reduces the SNR, or folded or deformed, which causes severe image distortion and renders the image quality unsatisfactory. In contrast, the RF coil assembly 600 conforms to the curved anatomy, increasing the SNR of the images and coverage of the subject with much reduced image distortion or artifacts. Because of the increased SNR, the image resolution may be increased, allowing high-resolution imaging of the subject with increased coverage. For example, the RF coil assembly 600 allows high-resolution imaging of a subject having a breast size of 40 DD, which is unavailable using the conventional breast RF coil 650 or a blanket flexible RF coil assembly.

The RF coil assembly 600 is light-weight. Further, because the RF coil assembly 600 conforms to the breasts 656 of the subject, the RF coil assembly 600 does not press on the breasts 656 when the subject lies down supine with the RF coil assembly 600 placed on the subject. In comparison, a blanket flexible coil assembly would press the breasts 656 with the weight of the coil and deform the breast, reducing the accuracy of locations of the tissue for biopsy or surgery planning. In addition, because the RF coil assembly 600 does not press the breasts 656 against the chest wall, the breasts 656 are not moved together with the chest wall. Therefore, the effects of cardiac and/or respiratory motions are reduced compared to scanning with a blanket flexible coil.

Because the RF coil loops 201 conform to the contour of the breasts 656, the RF coil assembly 600 may be used with a nonmagnetic bra customized for a subject to position the breasts 656 anteriorly toward the head of the subject. During a scan, the subject does not wear a regular bra, instead a nonmagnetic bra, and the RF coil assembly 600 is placed over the nonmagnetic bra. The nonmagnetic bra positions to the breast 656 anteriorly to reduce artifacts from fat in the abdominal region.

Figure 8:
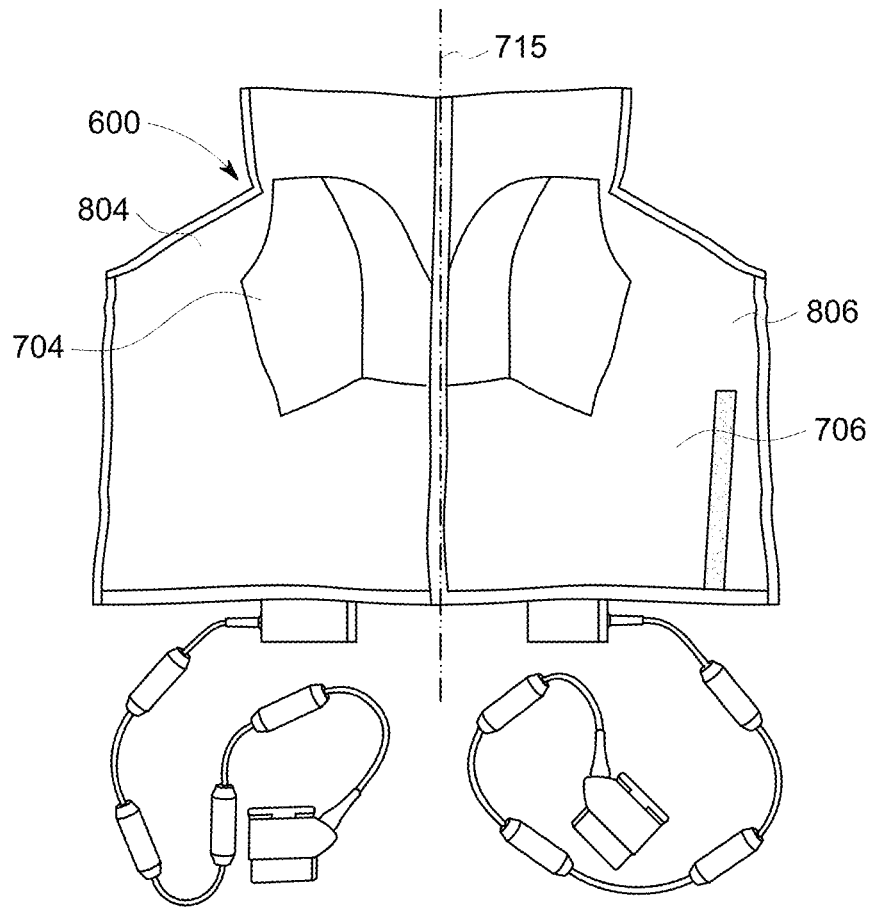
FIG. 8 shows another exemplary RF coil assembly.

FIG. 8 shows the RF coil assembly 600 is configured as two separable sections, the left and right portions 804, 806 included with the left section 704 of the RF coil array 700 and the right section 706 of the RF coil array 700, respectively (also see FIGS. 7A and 7B). The left portion 804 and the right portion 806 are referred herein as in FIG. 8, not the subject's left or right because the left portion 804 would be on the subject's right and the right portion 806 would be on the subject's left. The two portions 804, 806 are separable at the longitudinal midline 715. The two sections 704, 706 may be overlapped to reduce coupling by placing one section 704/706 partially over the other section 704/706. The two sections 704, 706, however, are not required to overlap with each other because the coupling electronics portions 203 reduce the mutual inductance coupling. Therefore, the spacing between the two sections 704, 706 may be adjusted to accommodate subjects who have unusually large distance between the breasts. Further, because the two portions 804, 806 do not have hardware between them, the subject may be imaged prone with the midline of the subject over the sternum bar 662 of the former or platform 658 (see FIG. 5) if a prone imaging is desired. The RF coil assembly 600 may also be used in imaging anatomies inside the chest or torso, such as cardiac imaging or abdominal imaging, by overlapping the two portions 804, 806 to largely reduce coupling and image artifacts. The RF coil array 700 may be used to with a posterior flexible blanket coil to further increase the coverage and acceleration factor. For example, the posterior coil may have 30 channels and the total number of channels may be 90 for a field of view (FOV), providing an increase acceleration factor while having a commensurate SNR.

Figure 9:
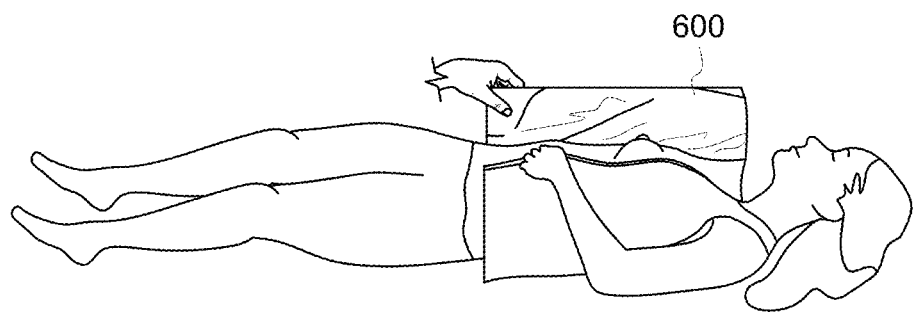
FIG. 9 shows an exemplary RF coil assembly allowing an easy access to the anatomy of the subject.

FIG. 9 shows the RF coil assembly 600 provides an easy access for biopsy or surgery. Because the RF coil assembly 600 is flexible, biopsy or surgery may be performed by simply lifting the RF coil assembly 600 away from the breast 656, thereby allowing a full access to the tissue and performance of screening and biopsy at the same scan session. Performing screening and biopsy at the same scan session increases the accuracy of biopsy because the subject has not moved or the subject's anatomy has not changed between screening and biopsy. In contrast, with the conventional breast RF coil 650, some part of the breast is not accessible. The subject may be moved to a different room or scheduled for a different session for biopsy. The anatomy of the subject may have changed between the imaging session and biopsy session. For example, the tumor may have been reduced or inflamed due to treatment. Further, the RF coil assembly 600 allows prone and supine imaging, thereby not limited to the awkward position of conducting biopsy prone. The RF coil assembly 600 is shown as being lifted at one side as an example. The RF coil assembly 600 may be lifted at any side, including the side adjacent to the back and close to the arm by detaching the back section such as the straps 601 (FIG. 6E) from the front or using an RF coil assembly 600 that does not have a back section. As a result, any part of the anatomy is reachable by the biopsy needle. For example, the inner breast is directly reachable, without the biopsy needle passing through an entire breast and causing unnecessary damage to the tissue, unlike when the conventional breast coil 650 is used (see FIG. 5). Because the RF coil assembly 600 is flexible, the RF coil assembly 600 can be easily placed back on the subject after the invention procedures for additional imaging if needed.

Although access to the breast is shown with the subject lying in a supine position, the RF coil assembly 600 may be used in prone intervention procedures, such as prone biopsies like when the conventional breast coil 650 is used (see FIG. 5). For example, the subject lies prone in the scanner with the two portions 804, 806 (FIG. 8) of the RF coil assembly 600 being placed in the cavities 652 of the platform 658 (FIG. 5). A side access may be provided by detaching the straps or using a RF coil assembly 600 that does not have a back section. Because the RF coil assembly 600 is flexible, even if the RF coil assembly 600 may have an armpit portion 752 or a side portion (FIG. 7C), the RF coil assembly may be moved to allow a side access.

Similarly, the RF coil assembly 600 allows the performance of imaging and surgery at the same scan session, which would be impractical if the conventional breast coil 650 is used. For example, the subject lies supine in an interventional MR system, being imaged with the RF coil assembly 600, and the surgeon has a full access to the breast and operate on the breast using the acquired images as guidance.

The curvature of the RF coil assembly 600 is adjustable. The RF coil loops 201 are attached to the lining 712. The RF coil loops 201, however, remain flexible in multiple dimensions and may be not fixedly connected to each other (see FIG. 7D). The RF coil loops 201 may be slidably movable relative to one another as the curvature of the lining 712 changes.

Figure 10:
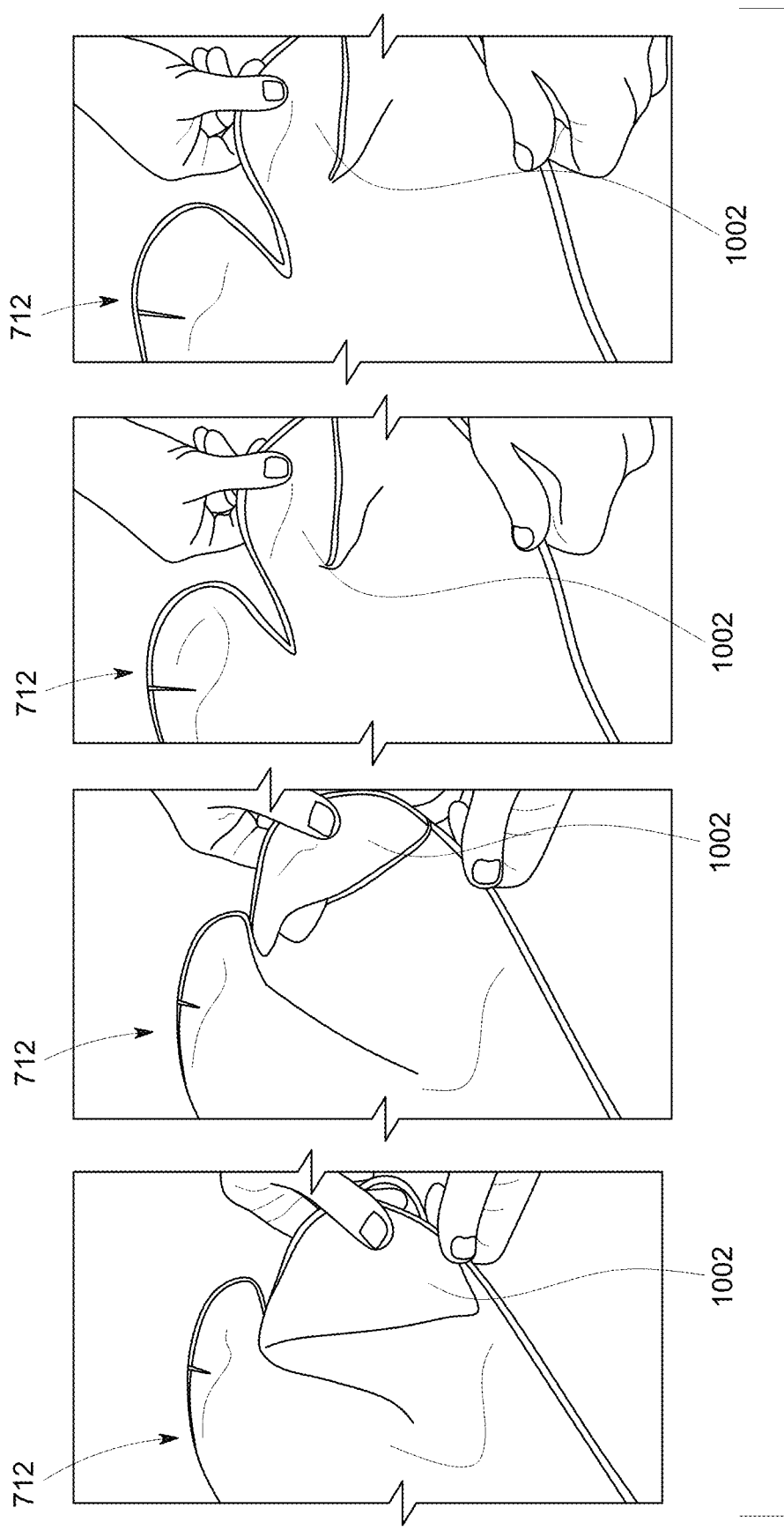
FIG. 10 shows that the curvature of an exemplary RF coil assembly is adjustable.

In addition, because the RF coil loops 201 are attached to the lining 712 at one or two sections of the RF coil loops 201 (not shown), the curvature of the RF coil assembly 600 may be changed by changing the curvature of the lining 712. The lining 712 may include an adjustable flap 1002 (FIG. 10). The curvature of the lining 712 is adjusted by moving the flap 1002. As a result, the curvature of the RF coil assembly 600 is adjusted as the RF coil loops 201 moves with the flap 1002.

Figure 11:
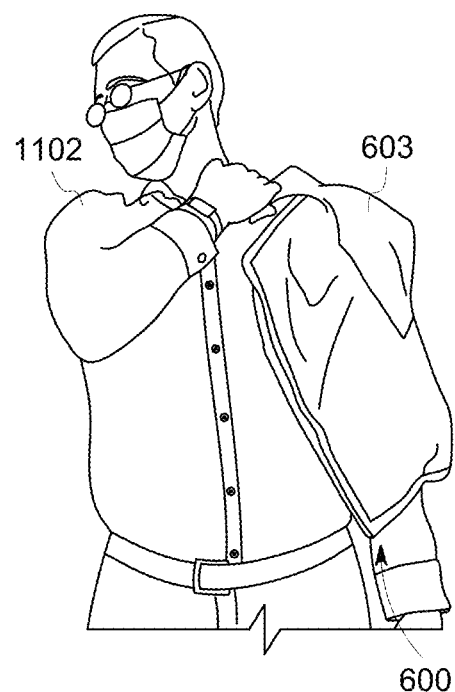
FIG. 11 shows an exemplary RF coil assembly as a shoulder coil.

The RF coil assembly 600 may be used to image any anatomy of the subject that is curved. FIG. 11 shows the RF coil assembly 600 is used as a shoulder coil to image a subject's shoulder. The contoured section 603 conforms to the curvature of the shoulder 1102 of the subject. In some embodiments, the RF coil assembly 600 is formed into a pair of shorts or pants for pelvic imaging, where the RF coil loops 201 conform to the curvature of the pelvic areas of the subject.

Figure 12:
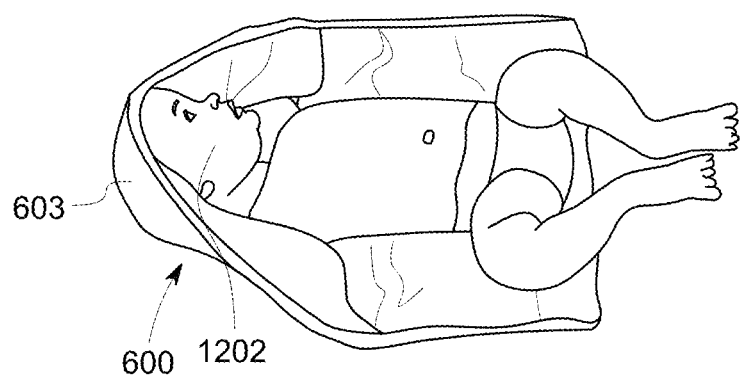
FIG. 12 shows an exemplary RF coil assembly as a pediatric head coil.

In another example, the RF coil assembly 600 is configured as a pediatric head coil (FIG. 12). A conventional head coil is rigid and may not be adjusted. A child has a much smaller head than an adult. The SNR of the signals from a child's head is, therefore, low if a conventional head coil is used, rendering the conventional head coil suboptimal for pediatric head imaging. Because the RF coil assembly 600 conforms to the curvature of the head, the SNR is largely increased if the child's head is imaged with the RF coil assembly 600. In addition, the head of a child, especially an infant, grows fast. The RF coil assembly 600 is suitable for scanning a growing head 1202 because the RF coil assembly 600 is flexible and/or the curvature of the RF coil assembly 600 is adjustable.

In parallel imaging, image acquisition may be accelerated by using multiple RF coils to augment the time consuming Fourier encoding. Acceleration factor R is defined as the ratio of the amount of k-space data required for a fully sampled image to the amount collected in the accelerated acquisition. For example, if every other line in the k-space is collected, the acquisition is accelerated by a factor $R=2$. An acceleration factor may be in more than one number for 3D scanning. For example, an acceleration factor of $3\times2$ is that the acceleration factor is 3 in the first phase-encoding direction and is 2 in the second phase-encoding direction such as in the slice direction. Because of the large number of coil loops 201 that the RF coil assembly 600 has, the acceleration factor may be increased.

Figure 13A:
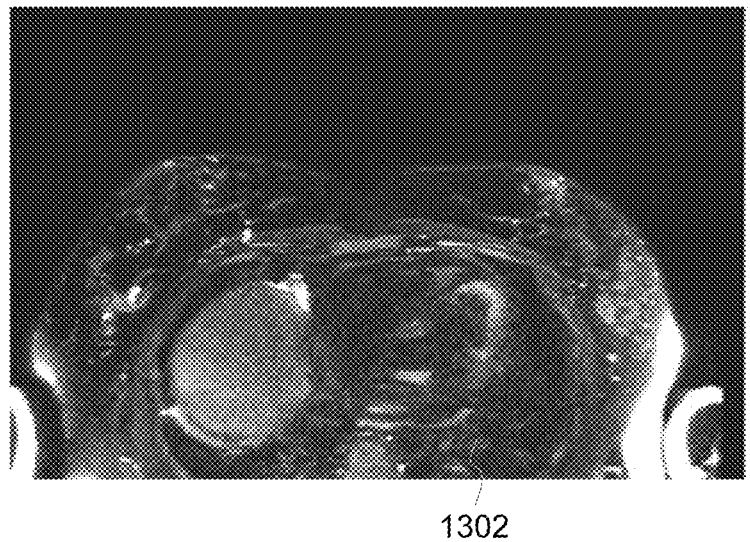
FIG. 13A is an MR image acquired using an exemplary RF coil assembly with an acceleration factor of 3.
Figure 13B:
FIG. 13B is another MR image acquired using the RF coil assembly for FIG. 13A with an acceleration factor of 5.

FIGS. 13A and 13B are images 1302, 1304 acquired using the RF coil assembly 600. The images 1302, 1304 are axial images of the chest area of the subject, acquired with a single shot fast spin echo (SSFSE) sequence. The image 1302 is acquired with an acceleration factor of 3, a maximum acceleration factor available for the conventional breast RF coil 650 on the system. In contrast, the maximum acceleration factor for the RF coil assembly 600 is 6 on the same system. The image 1304 is acquired with an acceleration factor of 5. The images 1302, 1304 not only include the breasts 656, but also include armpit areas. Fibroglandular tissue 1306 is visible in the images 1302, 1304. Compared to the image 1302, the image 1304 has an increased sharpness due to reduced T2 blurring resulted from a shortened echo train due to an increased acceleration factor. In addition, comparing the image 660 acquired by the conventional breast RF coil 650 (FIG. 5) with the images 1302, 1304, shape and tissue positions of the breast change significantly. Therefore, using a prone image acquired by a conventional breast RF coil 650 as guidance for supine biopsy or surgery planning would be impractical, while the RF coil assembly 600 allows acquisition of supine images for an increased accuracy in biopsy and surgery planning.

Figure 14A:
FIG. 14A is an image acquired using an exemplary RF coil assembly with an acceleration factor of 3×2.
Figure 14B:
FIG. 14B is an image acquired using the RF coil assembly for FIG. 14A with an acceleration factor of 4×2.
Figure 14C:
FIG. 14C is an image acquired using the RF coil assembly for FIG. 14A with an acceleration factor of 5×2.

FIGS. 14A-14C show images 1402, 1404, 1406 acquired using the RF coil assembly 600 with various acceleration factors. The images 1402, 1404, 1406 are acquired with a three dimension (3D) pulse sequence of liver acquisition with volume acceleration flex (LAVA-Flex). Scan parameters used are FOV of $40\times40$ cm, TR of 1.7 ms, TE of 1.7 ms, matrix size of $380\times380$, and 848 slices. The image 1402 is acquired with an acceleration factor of $3\times2$, resulting in the total scan time of 18 seconds. The image 1404 is acquired with an acceleration factor of $4\times2$, with a total scan time of 14 seconds. The image 1406 is acquired with an acceleration factor of $5\times2$, resulting in a total scan time of 12 seconds. The acceleration factor of the RF coil assembly 600 shown in FIGS. 7A-7G, which has 60 channels, may reach up to $5\times3$. The higher the acceleration factor, the shorter the scan time. 20 seconds is an acceptable duration of time for a person who has pulmonary issues such as pulmonary edema or bronco issues to hold breath. With the shortened time as described above, breath holding during scanning is not a challenge for subjects, when scanning with the RF coil assembly 600.

At least one technical effect of the systems and methods described herein includes (a) supine breast coil and scanning; (b) a torso coil that allows the scanning of nymph nodes under the armpit and on the upper chest; (c) a coil conforming to a contoured anatomy; (d) a breast coil of reduced cardiac and respiratory motion effects; (e) a coil having an increased acceleration factor; and (f) a coil allowing a full access to tissue and performance of imaging and biopsy/surgery at the same scan session; and (g) a breast coil separable into two halves.

Exemplary embodiments of assemblies, systems, and methods of RF coil assemblies are described above in detail. The systems and methods are not limited to the specific embodiments described herein but, rather, components of the systems and/or operations of the methods may be utilized independently and separately from other components and/or operations described herein. Further, the described components and/or operations may also be defined in, or used in combination with, other systems, methods, and/or devices, and are not limited to practice with only the systems described herein.

Although specific features of various embodiments of the invention may be shown in some drawings and not in others, this is for convenience only. In accordance with the principles of the invention, any feature of a drawing may be referenced and/or claimed in combination with any feature of any other drawing.

This written description uses examples to disclose the invention, including the best mode, and to enable any person skilled in the art to practice the invention, including making and using any devices or systems and performing any incorporated methods. The patentable scope of the invention is defined by the claims, and may include other examples that occur to those skilled in the art. Such other examples are intended to be within the scope of the claims if they have structural elements that do not differ from the literal language of the claims, or if they include equivalent structural elements with insubstantial differences from the literal language of the claims.

What is claimed is:

1. A supine torso radio frequency (RF) coil assembly for a magnetic resonance (MR) system, comprising:
    an RF coil array comprising:
        a plurality of RF coils each RF coil comprising:
            a coil loop that comprises a wire conductor, the wire conductor formed into the coil loop; and
            a coupling electronics portion coupled to the coil loop,
        wherein the plurality of RF coils form into a contoured portion, the contoured portion sized to receive at least part of a breast of a subject therein and having a predefined shape; and
    a lining including a contoured portion having the predefined shape,
    wherein the RF coil array is coupled to and distributed on the lining, the contoured portion of the RF coil array covering and conforming with the contoured portion of the lining.

2. The RF coil assembly of claim 1, further comprising two RF coil arrays separable from one another along a longitudinal midline and each having a contoured portion, wherein the lining is separable along the longitudinal midline and includes two contoured portions each covered by and conforming with one of the contoured portions of the RF coil arrays.

3. The RF coil assembly of claim 1, wherein the RF coil array further comprises an armpit portion positioned sideways away from the contoured portion in a first direction.

4. The RF coil assembly of claim 3, wherein the RF coil array further comprises an upper chest portion positioned away from the contoured portion in a second direction substantially perpendicular to the first direction.

5. The RF coil assembly of claim 4, wherein the RF coil array further comprises a lower torso portion positioned away from the contoured portion in a direction opposite to the second direction.

6. The RF coil assembly of claim 1, wherein the plurality of RF coils of the contoured portion are highly overlapped.

7. The RF coil assembly of claim 1, further comprising one or more straps, wherein the straps are configured to adjust fitting of the contoured portion of the RF coil array with the breast of the subject.

8. The RF coil assembly of claim 1, wherein the contoured portion of the RF coil array has an adjustable curvature.

9. The RF coil assembly of claim 1, wherein the coil loop is an integrated capacitor coil loop that comprises two parallel wire conductors and a dielectric material encapsulating and separating the two parallel wire conductors.

10. The RF coil assembly of claim 1, wherein the wire conductor comprises a plurality of strands.

11. The RF coil assembly of claim 1, wherein the coil loop comprises a plurality of turns formed by the wire conductor.

12. A radio frequency (RF) coil assembly for a magnetic resonance (MR) system, comprising:
    an RF coil array comprising:
        a plurality of RF coils each RF coil comprising:
            a coil loop that comprises a wire conductor, the wire conductor formed into the coil loop; and
            a coupling electronics portion electrically connected to the coil loop,
        wherein the plurality of RF coils form into a contoured portion, the contoured portion sized to receive at least part of a curved anatomy of a subject therein and having a predefined contour; and
    a lining including a contoured portion having the predefined contour,
    wherein the RF coil array is coupled to and distributed on the lining, the contoured portion of the RF coil array covering and conforming with the contoured portion of the lining.

13. The RF coil assembly of claim 12, wherein the contoured portion of the RF coil array is sized to receive at least part of a breast of the subject therein, the RF coil assembly further comprising two RF coil arrays separable from one another along a longitudinal midline and each having a contoured portion, wherein the lining is separable along the longitudinal midline and includes two contoured portions each covered by and conforming with one of the contoured portions of the RF coil arrays.

14. The RF coil assembly of claim 12, wherein the contoured portion of the RF coil array is sized to receive at least part of a breast of the subject therein, and the RF coil array further comprises an armpit portion positioned sideways away from the contoured portion in a first direction.

15. The RF coil assembly of claim 14, wherein the RF coil array further comprises an upper chest portion positioned away from the contoured portion in a second direction substantially perpendicular to the first direction.

16. The RF coil assembly of claim 12, wherein the RF coil assembly includes 60 RF coils and have 60 channels.

17. The RF coil assembly of claim 12, wherein the contoured portion of the RF coil array is sized to fit onto a head of a child.

18. The RF coil assembly of claim 12, wherein the contoured portion of the RF coil array is sized to fit over a shoulder of the subject.

19. The RF coil assembly of claim 12, wherein the wire conductor comprises a plurality of strands.

20. The RF coil assembly of claim 12, wherein the coil loop comprises a plurality of turns formed by the wire conductor.

\* \* \* \* \*